(12) United States Patent
Yang et al.

(10) Patent No.: US 10,865,391 B2
(45) Date of Patent: Dec. 15, 2020

(54) GLUTAMATE DEHYDROGENASE MUTANTS AND THEIR APPLICATION IN PREPARATION OF L-PHOSPHINOTHRICIN

(71) Applicant: ZHEJIANG UNIVERSITY, Zhejiang (CN)

(72) Inventors: Lirong Yang, Zhejiang (CN); Xinjian Yin, Zhejiang (CN); Jianping Wu, Zhejiang (CN); Gang Xu, Zhejiang (CN)

(73) Assignee: ZHEJIANG UNIVERSITY, Zhejiang (CN)

( * ) Notice: Subject to any disclaimer, the term of this patent is extended or adjusted under 35 U.S.C. 154(b) by 0 days.

(21) Appl. No.: 16/476,302

(22) PCT Filed: Sep. 12, 2018

(86) PCT No.: PCT/CN2018/105158
§ 371 (c)(1),
(2) Date: Jul. 8, 2019

(87) PCT Pub. No.: WO2019/169849
PCT Pub. Date: Sep. 12, 2019

(65) Prior Publication Data
US 2020/0102546 A1    Apr. 2, 2020

(30) Foreign Application Priority Data

Mar. 9, 2018 (CN) .......................... 2018 1 0194742

(51) Int. Cl.
*C12N 9/06* (2006.01)
*C12P 13/04* (2006.01)

(52) U.S. Cl.
CPC ............ *C12N 9/0016* (2013.01); *C12P 13/04* (2013.01); *C12Y 104/01002* (2013.01); *C12Y 104/01003* (2013.01); *C12Y 104/01004* (2013.01)

(58) Field of Classification Search
CPC .......... C12N 9/0016; C12Y 104/01003; C12Y 104/01002; C12Y 104/01; C12P 13/04
See application file for complete search history.

(56) References Cited

U.S. PATENT DOCUMENTS 4,265,654 A    5/1981 Takematsu et al.

FOREIGN PATENT DOCUMENTS

| CN | 106978453 |   | 7/2017 |         |
|----|-----------|---|--------|---------|
| CN | 106978453 A | * | 7/2017 | ...... C12P 13/04 |

OTHER PUBLICATIONS

Yin et al., Efficient reductive amination process for enantioselective synthesis of L-phosphinothricin applying engineered glutamate dehydrogenase. Appl. Microbiol. Biotechnol., 2018, vol. 102: 4425-4433. (Year: 2018).*
Lou et al., "Progresses in Biosynthesis of L-Phosphinothricin", Modern Agrochemicals, vol. 8, Issue 3, Jun. 2009, pp. 1-7.
Norbert M. W. Brunhuber et al., "The biochemistry and enzymology of amino acid dehydrogenases", Critical Reviews in Biochemistry and Molecular Biology, vol. 29, Issue 6, Feb. 1994, pp. 415-467.
IUPAC-IUB Joint Commission on Biochemical Nomenclature (JCBN), "Nomenclature and Symbolism for Amino Acids and Peptides",The FEBS Journal, vol. 138, Issue 1, Jan. 1984, pp. 9-37.
Abdelhamid Elbrghathi, "Structural Studies on dehydrogenases", Thesis of Doctor Degree, University of Shefield, Jul. 2014, pp. 1-232.
Shanshan Li et al., "Complete Genome Sequence of the Naphthalene-Degrading Pseudomonas putida Strain ND6", Journal of Bacteriology, vol. 194, No. 18, Sep. 2012, pp. 5154-5155.
WP_003856385.1, Genbank, "Multispecies: NADP-specific glutamate dehydrogenase [Corynebacterium]", Nov. 3, 2015, Available at: https://www.ncbi.nlm.nih.gov/protein/WP_003856385.1?report=gpwithparts&log$=seqview.
CAK13726.1, Genbank, "glutamate dehydrogenase, NADP-specific [Pseudomonas entomophila L48]", Feb. 27, 2015, Available at: https://www.ncbi.nlm.nih.gov/protein/CAK13726.1.
WP_012293812.1, Genbank, "NADP-specific glutamate dehydrogenase [Lysinibacillus sphaericus]", Aug. 4, 2017, Available at: https://www.ncbi.nlm.nih.gov/protein/WP_012293812.1.
KMY60667.1, Genbank, "glutamate dehydrogenase [Geobacillus stearothermophilus]", Jul. 21, 2015, Available at: https://www.ncbi.nlm.nih.gov/protein/KMY60667.1.
"International Search Report (Form PCT/ISA/210) of PCT/CN2018/105158," dated Dec. 19, 2018, pp. 1-6.

* cited by examiner

*Primary Examiner* — Ganapathirama Raghu
(74) *Attorney, Agent, or Firm* — JCIPRNET

(57) ABSTRACT

The present invention relates to glutamate dehydrogenase mutants and their application in preparation of L-phosphinothricin. The amino acid sequences of the glutamate dehydrogenase mutants are as shown in SEQ ID NO. 1-9, 11, 13, 15, 17-19 and 22. By means of molecular engineering, mutating the specific alanine in glutamate dehydrogenase substrate-binding pocket into glycine and/or mutating the specific valine in glutamate dehydrogenase substrate-binding pocket into alanine, the present invention has obtained NADPH-specific glutamate dehydrogenase mutants with high enzyme activity in catalyzing the substrate 2-oxo-4-[(hydroxy)(methyl)phosphinoyl]butyric acid or its salt for L-phosphinothricin preparation or NADH-specific glutamate dehydrogenase mutants with catalytic activity toward PPO; this has significantly improved substrate conversion, and increased the product concentration of the L-phosphinothricin preparation process.

6 Claims, 9 Drawing Sheets

Specification includes a Sequence Listing.

FIG. 7

SEQUENCE LISTING

```
<160> NUMBER OF SEQ ID NOS: 26

<210> SEQ ID NO 1
<211> LENGTH: 449
<212> TYPE: PRT
<213> ORGANISM: Artificial sequence
<220> FEATURE:
<223> OTHER INFORMATION: Pseudomonas putida glutamate dehydrogenase
      mutant

<400> SEQUENCE: 1

Met Ser Thr Met Ile Glu Ser Val Asp Asn Phe Leu Ala Arg Leu Lys
1               5                   10                  15

Gln Arg Asp Pro Gly Gln Pro Glu Phe His Gln Ala Val Glu Glu Val
            20                  25                  30

Leu Arg Thr Leu Trp Pro Phe Leu Glu Ala Asn Pro His Tyr Leu Gln
        35                  40                  45

Ser Gly Ile Leu Glu Arg Met Val Glu Pro Glu Arg Ala Val Leu Phe
    50                  55                  60

Arg Val Ser Trp Val Asp Asp Gln Gly Lys Val Gln Val Asn Arg Gly
65                  70                  75                  80

Tyr Arg Ile Gln Met Ser Ser Ala Ile Gly Pro Tyr Lys Gly Gly Leu
                85                  90                  95

Arg Phe His Pro Ser Val Asn Leu Ser Val Leu Lys Phe Leu Ala Phe
            100                 105                 110

Glu Gln Val Phe Lys Asn Ser Leu Thr Ser Leu Pro Met Gly Gly Gly
        115                 120                 125

Lys Gly Gly Ser Asp Phe Asp Pro Lys Gly Lys Ser Asp Ala Glu Val
    130                 135                 140
```

Met Arg Phe Cys Gln Ala Phe Met Ser Glu Leu Tyr Arg His Ile Gly
145                 150                 155                 160

Ala Asp Cys Asp Val Pro Gly Gly Asp Ile Gly Val Gly Ala Arg Glu
            165                 170                 175

Ile Gly Phe Met Phe Gly Gln Tyr Lys Arg Leu Ala Asn Gln Phe Thr
        180                 185                 190

Ser Val Leu Thr Gly Lys Gly Met Thr Tyr Gly Gly Ser Leu Ile Arg
    195                 200                 205

Pro Glu Ala Thr Gly Tyr Gly Cys Val Tyr Phe Ala Glu Glu Met Leu
210                 215                 220

Lys Arg Gln Asp Lys Arg Ile Asp Gly Arg Val Ala Val Ser Gly
225                 230                 235                 240

Ser Gly Asn Val Ala Gln Tyr Ala Ala Arg Lys Val Met Asp Leu Gly
            245                 250                 255

Gly Lys Val Ile Ser Leu Ser Asp Ser Glu Gly Thr Leu Tyr Ala Glu
        260                 265                 270

Ala Gly Leu Thr Asp Ala Gln Trp Asp Ala Leu Met Glu Leu Lys Asn
    275                 280                 285

Val Lys Arg Gly Arg Ile Ser Glu Leu Ala Gly Gln Phe Gly Leu Glu
290                 295                 300

Phe Arg Lys Gly Gln Thr Pro Trp Ser Leu Pro Cys Asp Ile Ala Leu
305                 310                 315                 320

Pro Cys Ala Thr Gln Asn Glu Leu Gly Ala Glu Asp Ala Arg Thr Leu
            325                 330                 335

Leu Arg Asn Gly Cys Ile Cys Val Ala Glu Gly Ala Asn Met Pro Thr
        340                 345                 350

Thr Leu Glu Ala Val Asp Ile Phe Leu Asp Ala Gly Ile Leu Tyr Ala
    355                 360                 365

Pro Gly Lys Ala Ser Asn Ala Gly Gly Val Ala Val Ser Gly Leu Glu
370                 375                 380

Met Ser Gln Asn Ala Met Arg Leu Leu Trp Thr Ala Gly Glu Val Asp
385                 390                 395                 400

Ser Lys Leu His Asn Ile Met Gln Ser Ile His His Ala Cys Val His
            405                 410                 415

Tyr Gly Glu Glu Ala Asp Gly Arg Ile Asn Tyr Val Lys Gly Ala Asn
        420                 425                 430

Ile Ala Gly Phe Val Lys Val Ala Asp Ala Met Leu Ala Gln Gly Val
    435                 440                 445

Val

<210> SEQ ID NO 2
<211> LENGTH: 449
<212> TYPE: PRT
<213> ORGANISM: Artificial
<220> FEATURE:
<223> OTHER INFORMATION: Pseudomonas putida glutamate dehydrogenase
      mutant

<400> SEQUENCE: 2

Met Ser Thr Met Ile Glu Ser Val Asp Asn Phe Leu Ala Arg Leu Lys
1               5                   10                  15

Gln Arg Asp Pro Gly Gln Pro Glu Phe His Gln Ala Val Glu Glu Val
            20                  25                  30

Leu Arg Thr Leu Trp Pro Phe Leu Glu Ala Asn Pro His Tyr Leu Gln
        35                  40                  45

```
Ser Gly Ile Leu Glu Arg Met Val Glu Pro Glu Arg Ala Val Leu Phe
 50                  55                  60

Arg Val Ser Trp Val Asp Asp Gln Gly Lys Val Gln Val Asn Arg Gly
 65                  70                  75                  80

Tyr Arg Ile Gln Met Ser Ser Ala Ile Gly Pro Tyr Lys Gly Gly Leu
                 85                  90                  95

Arg Phe His Pro Ser Val Asn Leu Ser Val Leu Lys Phe Leu Ala Phe
                100                 105                 110

Glu Gln Val Phe Lys Asn Ser Leu Thr Ser Leu Pro Met Gly Gly Gly
            115                 120                 125

Lys Gly Gly Ser Asp Phe Asp Pro Lys Gly Lys Ser Asp Ala Glu Val
130                 135                 140

Met Arg Phe Cys Gln Ala Phe Met Ser Glu Leu Tyr Arg His Ile Gly
145                 150                 155                 160

Ala Asp Cys Asp Val Pro Ala Gly Asp Ile Gly Val Gly Ala Arg Glu
                165                 170                 175

Ile Gly Phe Met Phe Gly Gln Tyr Lys Arg Leu Ala Asn Gln Phe Thr
                180                 185                 190

Ser Val Leu Thr Gly Lys Gly Met Thr Tyr Gly Gly Ser Leu Ile Arg
            195                 200                 205

Pro Glu Ala Thr Gly Tyr Gly Cys Val Tyr Phe Ala Glu Glu Met Leu
210                 215                 220

Lys Arg Gln Asp Lys Arg Ile Asp Gly Arg Arg Val Ala Val Ser Gly
225                 230                 235                 240

Ser Gly Asn Val Ala Gln Tyr Ala Ala Arg Lys Val Met Asp Leu Gly
                245                 250                 255

Gly Lys Val Ile Ser Leu Ser Asp Ser Glu Gly Thr Leu Tyr Ala Glu
                260                 265                 270

Ala Gly Leu Thr Asp Ala Gln Trp Asp Ala Leu Met Glu Leu Lys Asn
            275                 280                 285

Val Lys Arg Gly Arg Ile Ser Glu Leu Ala Gly Gln Phe Gly Leu Glu
290                 295                 300

Phe Arg Lys Gly Gln Thr Pro Trp Ser Leu Pro Cys Asp Ile Ala Leu
305                 310                 315                 320

Pro Cys Ala Thr Gln Asn Glu Leu Gly Ala Glu Asp Ala Arg Thr Leu
                325                 330                 335

Leu Arg Asn Gly Cys Ile Cys Val Ala Glu Gly Ala Asn Met Pro Thr
                340                 345                 350

Thr Leu Glu Ala Val Asp Ile Phe Leu Asp Ala Gly Ile Leu Tyr Ala
            355                 360                 365

Pro Gly Lys Ala Ser Asn Ala Gly Gly Ala Ala Val Ser Gly Leu Glu
370                 375                 380

Met Ser Gln Asn Ala Met Arg Leu Leu Trp Thr Ala Gly Glu Val Asp
385                 390                 395                 400

Ser Lys Leu His Asn Ile Met Gln Ser Ile His His Ala Cys Val His
                405                 410                 415

Tyr Gly Glu Glu Ala Asp Gly Arg Ile Asn Tyr Val Lys Gly Ala Asn
                420                 425                 430

Ile Ala Gly Phe Val Lys Val Ala Asp Ala Met Leu Ala Gln Gly Val
            435                 440                 445

Val
```

```
<210> SEQ ID NO 3
<211> LENGTH: 447
<212> TYPE: PRT
<213> ORGANISM: Artificial
<220> FEATURE:
<223> OTHER INFORMATION: Corynebacterium glutamicum glutamate
      dehydrogenase mutant

<400> SEQUENCE: 3
```

Met Thr Val Asp Glu Gln Val Ser Asn Tyr Tyr Asp Met Leu Leu Lys
1               5                   10                  15

Arg Asn Ala Gly Glu Pro Glu Phe His Gln Ala Val Ala Glu Val Leu
            20                  25                  30

Glu Ser Leu Lys Ile Val Leu Glu Lys Asp Pro His Tyr Ala Asp Tyr
        35                  40                  45

Gly Leu Ile Gln Arg Leu Cys Glu Pro Glu Arg Gln Leu Ile Phe Arg
    50                  55                  60

Val Pro Trp Val Asp Asp Gln Gly Gln Val His Val Asn Arg Gly Phe
65              70                  75                  80

Arg Val Gln Phe Asn Ser Ala Leu Gly Pro Tyr Lys Gly Gly Leu Arg
                85                  90                  95

Phe His Pro Ser Val Asn Leu Gly Ile Val Lys Phe Leu Gly Phe Glu
            100                 105                 110

Gln Ile Phe Lys Asn Ser Leu Thr Gly Leu Pro Ile Gly Gly Gly Lys
        115                 120                 125

Gly Gly Ser Asp Phe Asp Pro Lys Gly Lys Ser Asp Leu Glu Ile Met
    130                 135                 140

Arg Phe Cys Gln Ser Phe Met Thr Glu Leu His Arg His Ile Gly Glu
145                 150                 155                 160

Tyr Arg Asp Val Pro Gly Gly Asp Ile Gly Val Gly Gly Arg Glu Ile
                165                 170                 175

Gly Tyr Leu Phe Gly His Tyr Arg Arg Met Ala Asn Gln His Glu Ser
            180                 185                 190

Gly Val Leu Thr Gly Lys Gly Leu Thr Trp Gly Gly Ser Leu Val Arg
        195                 200                 205

Thr Glu Ala Thr Gly Tyr Gly Cys Val Tyr Phe Val Ser Glu Met Ile
    210                 215                 220

Lys Ala Lys Gly Glu Ser Ile Ser Gly Gln Lys Ile Ile Val Ser Gly
225                 230                 235                 240

Ser Gly Asn Val Ala Thr Tyr Ala Ile Glu Lys Ala Gln Glu Leu Gly
                245                 250                 255

Ala Thr Val Ile Gly Phe Ser Asp Ser Ser Gly Trp Val His Thr Pro
            260                 265                 270

Asn Gly Val Asp Val Ala Lys Leu Arg Glu Ile Lys Glu Val Arg Arg
        275                 280                 285

Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
            340                 345                 350

Glu Ala Val Glu Val Phe Arg Glu Arg Asp Ile Arg Phe Gly Pro Gly
        355                 360                 365

```
Lys Ala Asn Ala Gly Gly Val Ala Thr Ser Ala Leu Glu Met Gln
    370             375                 380
Gln Asn Ala Ser Arg Asp Ser Trp Ser Phe Glu Tyr Thr Asp Glu Arg
385                 390                 395                 400
Leu Gln Val Ile Met Lys Asn Ile Phe Lys Thr Cys Ala Glu Thr Ala
                405                 410                 415
Ala Glu Tyr Gly His Glu Asn Asp Tyr Val Val Gly Ala Asn Ile Ala
            420                 425                 430
Gly Phe Lys Lys Val Ala Asp Ala Met Leu Ala Gln Gly Val Ile
            435                 440                 445

<210> SEQ ID NO 4
<211> LENGTH: 447
<212> TYPE: PRT
<213> ORGANISM: Artificial
<220> FEATURE:
<223> OTHER INFORMATION: Corynebacterium glutamicum glutamate
      dehydrogenase mutant

<400> SEQUENCE: 4

Met Thr Val Asp Glu Gln Val Ser Asn Tyr Tyr Asp Met Leu Leu Lys
1               5                   10                  15
Arg Asn Ala Gly Glu Pro Glu Phe His Gln Ala Val Ala Glu Val Leu
                20                  25                  30
Glu Ser Leu Lys Ile Val Leu Glu Lys Asp Pro His Tyr Ala Asp Tyr
            35                  40                  45
Gly Leu Ile Gln Arg Leu Cys Glu Pro Glu Arg Gln Leu Ile Phe Arg
        50                  55                  60
Val Pro Trp Val Asp Asp Gln Gly Gln Val His Val Asn Arg Gly Phe
65                  70                  75                  80
Arg Val Gln Phe Asn Ser Ala Leu Gly Pro Tyr Lys Gly Gly Leu Arg
                85                  90                  95
Phe His Pro Ser Val Asn Leu Gly Ile Val Lys Phe Leu Gly Phe Glu
            100                 105                 110
Gln Ile Phe Lys Asn Ser Leu Thr Gly Leu Pro Ile Gly Gly Gly Lys
        115                 120                 125
Gly Gly Ser Asp Phe Asp Pro Lys Gly Lys Ser Asp Leu Glu Ile Met
130                 135                 140
Arg Phe Cys Gln Ser Phe Met Thr Glu Leu His Arg His Ile Gly Glu
145                 150                 155                 160
Tyr Arg Asp Val Pro Ala Gly Asp Ile Gly Val Gly Gly Arg Glu Ile
                165                 170                 175
Gly Tyr Leu Phe Gly His Tyr Arg Arg Met Ala Asn Gln His Glu Ser
            180                 185                 190
Gly Val Leu Thr Gly Lys Gly Leu Thr Trp Gly Gly Ser Leu Val Arg
        195                 200                 205
Thr Glu Ala Thr Gly Tyr Gly Cys Val Tyr Phe Val Ser Glu Met Ile
210                 215                 220
Lys Ala Lys Gly Glu Ser Ile Ser Gly Gln Lys Ile Ile Val Ser Gly
225                 230                 235                 240
Ser Gly Asn Val Ala Thr Tyr Ala Ile Glu Lys Ala Gln Glu Leu Gly
                245                 250                 255
Ala Thr Val Ile Gly Phe Ser Asp Ser Ser Gly Trp Val His Thr Pro
            260                 265                 270
Asn Gly Val Asp Val Ala Lys Leu Arg Glu Ile Lys Glu Val Arg Arg
        275                 280                 285
```

```
Ala Arg Val Ser Val Tyr Ala Asp Glu Val Glu Gly Ala Thr Tyr His
    290                 295                 300

Thr Asp Gly Ser Ile Trp Asp Leu Lys Cys Asp Ile Ala Leu Pro Cys
305                 310                 315                 320

Ala Thr Gln Asn Glu Leu Asn Gly Glu Asn Ala Lys Thr Leu Ala Asp
                325                 330                 335

Asn Gly Cys Arg Phe Val Ala Glu Gly Ala Asn Met Pro Ser Thr Pro
                340                 345                 350

Glu Ala Val Glu Val Phe Arg Glu Arg Asp Ile Arg Phe Gly Pro Gly
            355                 360                 365

Lys Ala Ala Asn Ala Gly Gly Ala Ala Thr Ser Ala Leu Glu Met Gln
    370                 375                 380

Gln Asn Ala Ser Arg Asp Ser Trp Ser Phe Glu Tyr Thr Asp Glu Arg
385                 390                 395                 400

Leu Gln Val Ile Met Lys Asn Ile Phe Lys Thr Cys Ala Glu Thr Ala
                405                 410                 415

Ala Glu Tyr Gly His Glu Asn Asp Tyr Val Val Gly Ala Asn Ile Ala
                420                 425                 430

Gly Phe Lys Lys Val Ala Asp Ala Met Leu Ala Gln Gly Val Ile
    435                 440                 445

<210> SEQ ID NO 5
<211> LENGTH: 446
<212> TYPE: PRT
<213> ORGANISM: Artificial
<220> FEATURE:
<223> OTHER INFORMATION: Pseudomonas entomophila glutamate dehydrogenase
      mutant

<400> SEQUENCE: 5

Met Ile Glu Ser Val Asp His Phe Leu Ala Arg Leu Gln Gln Arg Asp
1               5                   10                  15

Pro Ala Gln Pro Glu Phe His Gln Ala Val Glu Glu Val Leu Arg Ser
            20                  25                  30

Leu Trp Pro Phe Leu Glu Gln Asn Pro His Tyr Leu Glu Ala Gly Ile
        35                  40                  45

Leu Glu Arg Met Val Glu Pro Glu Arg Ala Val Leu Phe Arg Val Ser
50                  55                  60

Trp Val Asp Asp Gln Gly Lys Val Gln Val Asn Arg Gly Tyr Arg Ile
65                  70                  75                  80

Gln Met Ser Ser Ala Ile Gly Pro Tyr Lys Gly Gly Leu Arg Phe His
                85                  90                  95

Pro Ser Val Asn Leu Gly Val Leu Lys Phe Leu Ala Phe Glu Gln Val
            100                 105                 110

Phe Lys Asn Ser Leu Thr Ser Leu Pro Met Gly Gly Gly Lys Gly Gly
        115                 120                 125

Ser Asp Phe Asp Pro Lys Gly Lys Ser Asp Ala Glu Val Met Arg Phe
    130                 135                 140

Cys Gln Ala Phe Met Ser Glu Leu Tyr Arg His Ile Gly Ala Asp Leu
145                 150                 155                 160

Asp Val Pro Gly Gly Asp Ile Gly Val Gly Ala Arg Glu Ile Gly Phe
                165                 170                 175

Leu Phe Gly Gln Tyr Lys Arg Leu Ala Asn Gln Phe Thr Ser Val Leu
            180                 185                 190

Thr Gly Lys Gly Met Thr Tyr Gly Gly Ser Leu Ile Arg Pro Glu Ala
```

```
              195                 200                 205
Thr Gly Tyr Gly Cys Val Tyr Phe Ala Glu Glu Met Leu Lys Arg Gln
            210                 215                 220
Glu Gln Arg Ile Asp Gly Arg Arg Val Ala Ile Ser Gly Ser Gly Asn
225                 230                 235                 240
Val Ala Gln Tyr Ala Ala Arg Lys Val Met Asp Leu Gly Gly Lys Val
                245                 250                 255
Ile Ser Leu Ser Asp Ser Glu Gly Thr Leu Phe Cys Glu Ala Gly Leu
            260                 265                 270
Thr Asp Glu Gln Trp Asp Ala Leu Met Glu Leu Lys Asn Val Lys Arg
            275                 280                 285
Gly Arg Ile Ser Glu Leu Ala Gly Arg Phe Gly Leu Glu Phe Arg Lys
            290                 295                 300
Gly Gln Thr Pro Trp Ser Leu Ala Cys Asp Ile Ala Leu Pro Cys Ala
305                 310                 315                 320
Thr Gln Asn Glu Leu Asn Ala Asp Asp Ala Arg Thr Leu Leu Arg Asn
                325                 330                 335
Gly Cys Ile Cys Val Ala Glu Gly Ala Asn Met Pro Thr Thr Leu Asp
            340                 345                 350
Ala Val Asp Ile Phe Ile Glu Ala Gly Ile Leu Tyr Ala Pro Gly Lys
            355                 360                 365
Ala Ser Asn Ala Gly Gly Val Ala Val Ser Gly Leu Glu Met Ser Gln
            370                 375                 380
Asn Ala Met Arg Leu Leu Trp Thr Ala Gly Glu Val Asp Ser Lys Leu
385                 390                 395                 400
His His Ile Met Gln Ser Ile His His Val Cys Val His Tyr Gly Glu
                405                 410                 415
Glu Ala Asp Gly Arg Ile Asn Tyr Val Lys Gly Ala Asn Ile Ala Gly
            420                 425                 430
Phe Val Lys Val Ala Asp Ala Met Leu Ala Gln Gly Val Val
            435                 440                 445

<210> SEQ ID NO 6
<211> LENGTH: 446
<212> TYPE: PRT
<213> ORGANISM: Artificial
<220> FEATURE:
<223> OTHER INFORMATION: Pseudomonas entomophila glutamate dehydrogenase
      mutant

<400> SEQUENCE: 6

Met Ile Glu Ser Val Asp His Phe Leu Ala Arg Leu Gln Gln Arg Asp
1               5                   10                  15
Pro Ala Gln Pro Glu Phe His Gln Ala Val Glu Glu Val Leu Arg Ser
            20                  25                  30
Leu Trp Pro Phe Leu Glu Gln Asn Pro His Tyr Leu Glu Ala Gly Ile
        35                  40                  45
Leu Glu Arg Met Val Glu Pro Glu Arg Ala Val Leu Phe Arg Val Ser
    50                  55                  60
Trp Val Asp Asp Gln Gly Lys Val Gln Val Asn Arg Gly Tyr Arg Ile
65                  70                  75                  80
Gln Met Ser Ser Ala Ile Gly Pro Tyr Lys Gly Gly Leu Arg Phe His
                85                  90                  95
Pro Ser Val Asn Leu Gly Val Leu Lys Phe Leu Ala Phe Glu Gln Val
            100                 105                 110
```

-continued

```
Phe Lys Asn Ser Leu Thr Ser Leu Pro Met Gly Gly Gly Lys Gly Gly
        115                 120                 125

Ser Asp Phe Asp Pro Lys Gly Lys Ser Asp Ala Glu Val Met Arg Phe
    130                 135                 140

Cys Gln Ala Phe Met Ser Glu Leu Tyr Arg His Ile Gly Ala Asp Leu
145                 150                 155                 160

Asp Val Pro Ala Gly Asp Ile Gly Val Gly Ala Arg Glu Ile Gly Phe
                165                 170                 175

Leu Phe Gly Gln Tyr Lys Arg Leu Ala Asn Gln Phe Thr Ser Val Leu
            180                 185                 190

Thr Gly Lys Gly Met Thr Tyr Gly Gly Ser Leu Ile Arg Pro Glu Ala
        195                 200                 205

Thr Gly Tyr Gly Cys Val Tyr Phe Ala Glu Glu Met Leu Lys Arg Gln
    210                 215                 220

Glu Gln Arg Ile Asp Gly Arg Arg Val Ala Ile Ser Gly Ser Gly Asn
225                 230                 235                 240

Val Ala Gln Tyr Ala Ala Arg Lys Val Met Asp Leu Gly Gly Lys Val
                245                 250                 255

Ile Ser Leu Ser Asp Ser Glu Gly Thr Leu Phe Cys Glu Ala Gly Leu
            260                 265                 270

Thr Asp Glu Gln Trp Asp Ala Leu Met Glu Leu Lys Asn Val Lys Arg
        275                 280                 285

Gly Arg Ile Ser Glu Leu Ala Gly Arg Phe Gly Leu Glu Phe Arg Lys
    290                 295                 300

Gly Gln Thr Pro Trp Ser Leu Ala Cys Asp Ile Ala Leu Pro Cys Ala
305                 310                 315                 320

Thr Gln Asn Glu Leu Asn Ala Asp Asp Ala Arg Thr Leu Leu Arg Asn
                325                 330                 335

Gly Cys Ile Cys Val Ala Glu Gly Ala Asn Met Pro Thr Thr Leu Asp
            340                 345                 350

Ala Val Asp Ile Phe Ile Glu Ala Gly Ile Leu Tyr Ala Pro Gly Lys
        355                 360                 365

Ala Ser Asn Ala Gly Gly Ala Ala Val Ser Gly Leu Glu Met Ser Gln
    370                 375                 380

Asn Ala Met Arg Leu Leu Trp Thr Ala Gly Glu Val Asp Ser Lys Leu
385                 390                 395                 400

His His Ile Met Gln Ser Ile His His Val Cys Val His Tyr Gly Glu
                405                 410                 415

Glu Ala Asp Gly Arg Ile Asn Tyr Val Lys Gly Ala Asn Ile Ala Gly
            420                 425                 430

Phe Val Lys Val Ala Asp Ala Met Leu Ala Gln Gly Val Val
        435                 440                 445
```

<210> SEQ ID NO 7
<211> LENGTH: 457
<212> TYPE: PRT
<213> ORGANISM: Artificial
<220> FEATURE:
<223> OTHER INFORMATION: Lysinibacillus sphaericus glutamate dehydrogenase mutant

<400> SEQUENCE: 7

```
Met Thr Ile Thr Thr Val Ser Asn Glu Gln Leu Ala Lys Glu Tyr Val
1               5                   10                  15

Asp Gly Val Phe Glu Gln Leu Lys Gln Gln Asn Cys His Gln Ala Glu
            20                  25                  30

Phe Leu Gln Ala Ala Glu Glu Ile Phe Ile Ser Leu Val Pro Val Phe
            35                  40                  45

Val Gln His Pro Glu Tyr Ile Lys Ala Asn Ile Leu Ser Arg Ile Val
50                  55                  60

Glu Pro Asp Arg Ile Ile Ser Phe Arg Val Ala Trp Gln Asp Asp His
65                  70                  75                  80

Asn Gln Val Gln Val Asn Arg Gly Tyr Arg Val Gln Tyr Ser Asn Val
                85                  90                  95

Met Gly Pro Tyr Lys Gly Gly Leu Arg Phe His Pro Ser Val Asn Glu
                100                 105                 110

Ser Ile Ile Lys Phe Leu Gly Phe Glu Gln Ile Phe Lys Asn Ala Leu
                115                 120                 125

Thr Gly Gln Pro Ile Gly Gly Gly Lys Gly Gly Ser Asn Phe Asp Pro
                130                 135                 140

Lys Gly Lys Ser Asp Ser Glu Ile Met Arg Phe Cys Gln Ala Phe Met
145                 150                 155                 160

Thr Glu Leu Tyr Arg His Ile Gly Pro Asp Val Asp Val Pro Gly Gly
                165                 170                 175

Asp Ile Gly Val Gly Ala Arg Glu Val Gly Tyr Leu Trp Gly Gln Tyr
                180                 185                 190

Lys Arg Leu Thr Lys Ala Ser Glu Ser Gly Val Leu Thr Gly Lys Thr
                195                 200                 205

Pro Gly Tyr Gly Gly Ser Leu Ala Arg Lys Glu Ala Thr Gly Tyr Gly
                210                 215                 220

Thr Val Tyr Phe Val Asn Glu Met Leu Lys Asp Val Asn Asp Ser Phe
225                 230                 235                 240

Glu Gly Lys Thr Val Val Ser Gly Ser Gly Asn Val Ser Thr Tyr
                245                 250                 255

Ala Ile Glu Lys Ala Gln Gln Tyr Gly Ala Lys Val Val Ala Cys Ser
                260                 265                 270

Asp Ser Ser Gly Tyr Ile Tyr Asp Pro Glu Gly Leu Asp Leu Asp Val
                275                 280                 285

Ile Lys Glu Ile Lys Glu Val Lys Gly Asp Arg Ile Ser Thr Tyr Val
                290                 295                 300

Ser Tyr Arg Pro Asn Ala Thr Phe Thr Asn Gly Cys Thr Gly Ile Trp
305                 310                 315                 320

Thr Ile Pro Cys Asp Ile Ala Leu Pro Cys Ala Thr Gln Asn Glu Ile
                325                 330                 335

Asn Gly Glu Ser Ala Arg Thr Leu Ile Ser Asn Gly Val Lys Ala Ile
                340                 345                 350

Gly Glu Gly Ala Asn Met Pro Ser Asp Leu Glu Ala Ile Asn Glu Phe
                355                 360                 365

Leu Asn Ala Gly Val Leu Phe Gly Pro Ala Lys Ala Ala Asn Ala Gly
                370                 375                 380

Gly Val Ala Val Ser Ala Leu Glu Met Ala Gln Asp Ser Ser Arg Val
385                 390                 395                 400

Phe Trp Ser Phe Glu Glu Val Asp Ala Lys Leu His Gln Ile Met Lys
                405                 410                 415

Asp Ile Tyr Ser Asp Ser Lys Ala Ala Ala Glu Lys Tyr Gly Phe Pro
                420                 425                 430

Gly Asn Leu Val Met Gly Ala Asn Ile Ala Gly Phe Ile Lys Val Ala
                435                 440                 445

```
Asp Gly Met Leu Thr Glu Gly Ile Tyr
    450                 455
```

<210> SEQ ID NO 8
<211> LENGTH: 457
<212> TYPE: PRT
<213> ORGANISM: Artificial
<220> FEATURE:
<223> OTHER INFORMATION: Lysinibacillus sphaericus glutamate
      dehydrogenase mutant

<400> SEQUENCE: 8

```
Met Thr Ile Thr Thr Val Ser Asn Glu Gln Leu Ala Lys Glu Tyr Val
1               5                   10                  15

Asp Gly Val Phe Glu Gln Leu Lys Gln Gln Asn Cys His Gln Ala Glu
            20                  25                  30

Phe Leu Gln Ala Ala Glu Glu Ile Phe Ile Ser Leu Val P

```
Gly Glu Gly Ala Asn Met Pro Ser Asp Leu Glu Ala Ile Asn Glu Phe
            355                 360                 365
Leu Asn Ala Gly Val Leu Phe Gly Pro Ala Lys Ala Ala Asn Ala Gly
        370                 375                 380
Gly Ala Ala Val Ser Ala Leu Glu Met Ala Gln Asp Ser Ser Arg Val
385                 390                 395                 400
Phe Trp Ser Phe Glu Glu Val Asp Ala Lys Leu His Gln Ile Met Lys
                405                 410                 415
Asp Ile Tyr Ser Asp Ser Lys Ala Ala Glu Lys Tyr Gly Phe Pro
            420                 425                 430
Gly Asn Leu Val Met Gly Ala Asn Ile Ala Gly Phe Ile Lys Val Ala
            435                 440                 445
Asp Gly Met Leu Thr Glu Gly Ile Tyr
        450                 455

<210> SEQ ID NO 9
<211> LENGTH: 423
<212> TYPE: PRT
<213> ORGANISM: Artificial
<220> FEATURE:
<223> OTHER INFORMATION: Geobacillus stearothermophilus glutamate
      dehydrogenase mutant

<400> SEQUENCE: 9

Met Ala Ala Asp Lys His Thr Glu Glu Lys Gly Gln Gln Asp Asp Val
1               5                   10                  15
Leu Ala Ser Thr Gln Ile Val Ile His Arg Ala Leu Glu Lys Leu Gly
            20                  25                  30
Tyr Pro Glu Glu Val Tyr Glu Leu Leu Lys Glu Pro Ile Arg Val Leu
        35                  40                  45
Thr Val Arg Ile Pro Val Arg Met Asp Asp Gly Ser Val Lys Ile Phe
50                  55                  60
Thr Gly Tyr Arg Ala Gln His Asn Asp Ala Val Gly Pro Thr Lys Gly
65                  70                  75                  80
Gly Val Arg Phe His Pro Asp Val Thr Glu Arg Glu Val Lys Ala Leu
                85                  90                  95
Ser Ile Trp Met Ser Leu Lys Cys Gly Ile Val Asp Leu Pro Tyr Gly
            100                 105                 110
Gly Gly Lys Gly Gly Ile Val Cys Asp Pro Arg Thr Met Ser Phe Arg
        115                 120                 125
Glu Leu Glu Arg Leu Ser Arg Gly Tyr Val Arg Ala Ile Ser Gln Ile
    130                 135                 140
Val Gly Pro Thr Lys Asp Ile Pro Gly Pro Asp Val Phe Thr Asn Ser
145                 150                 155                 160
Gln Ile Met Ala Trp Met Met Asp Glu Tyr Ser Arg Ile Arg Glu Phe
                165                 170                 175
Asp Ser Pro Gly Phe Ile Thr Gly Lys Pro Leu Val Leu Gly Gly Ser
            180                 185                 190
His Gly Arg Glu Thr Ala Thr Ala Lys Gly Val Thr Ile Cys Ile Arg
        195                 200                 205
Glu Ala Ala Lys Lys Arg Gly Leu Ser Leu Glu Gly Ala Arg Val Val
    210                 215                 220
Val Gln Gly Phe Gly Asn Ala Gly Ser Tyr Leu Ala Lys Phe Leu His
225                 230                 235                 240
Asp Ala Gly Ala Lys Val Val Gly Ile Ser Asp Val Tyr Gly Ala Leu
```

```
                        245                 250                 255

Tyr Asp Pro Asn Gly Leu Asp Ile Asp Tyr Leu Leu Glu Arg Arg Asp
            260                 265                 270

Ser Phe Gly Thr Val Thr Lys Leu Phe Lys Asn Thr Ile Ser Asn Lys
            275                 280                 285

Glu Leu Leu Glu Leu Asp Cys Asp Ile Leu Val Pro Ala Ala Ile Glu
            290                 295                 300

Asn Gln Ile Thr Ala Glu Asn Ala Pro Arg Ile Lys Ala Ser Ile Val
305                 310                 315                 320

Val Glu Ala Ala Asn Gly Pro Thr Thr Leu Glu Ala Thr Glu Ile Leu
                325                 330                 335

Thr Gln Arg Gly Ile Leu Leu Val Pro Asp Val Leu Ala Ser Ala Gly
            340                 345                 350

Gly Val Thr Val Ser Tyr Phe Glu Trp Val Gln Asn Asn Gln Gly Tyr
            355                 360                 365

Tyr Trp Thr Glu Glu Val Glu Gln Arg Leu Glu Lys Val Met Val
            370                 375                 380

Lys Ala Phe Asn Asn Val Tyr Glu Met Ala Gln Thr Arg Arg Val Asp
385                 390                 395                 400

Met Arg Leu Ala Ala Tyr Met Val Gly Val Arg Lys Met Ala Glu Ala
                405                 410                 415

Cys Arg Phe Arg Gly Trp Val
            420

<210> SEQ ID NO 10
<211> LENGTH: 423
<212> TYPE: PRT
<213> ORGANISM: Artificial
<220> FEATURE:
<223> OTHER INFORMATION: Geobacillus stearothermophilus glutamate
      dehydrogenase mutant

<400> SEQUENCE: 10

Met Ala Ala Asp Lys His Thr Glu Glu Lys Gly Gln Gln Asp Asp Val
1               5                   10                  15

Leu Ala Ser Thr Gln Ile Val Ile His Arg Ala Leu Glu Lys Leu Gly
                20                  25                  30

Tyr Pro Glu Glu Val Tyr Glu Leu Leu Lys Glu Pro Ile Arg Val Leu
            35                  40                  45

Thr Val Arg Ile Pro Val Arg Met Asp Asp Gly Ser Val Lys Ile Phe
        50                  55                  60

Thr Gly Tyr Arg Ala Gln His Asn Asp Ala Val Gly Pro Thr Lys Gly
65                  70                  75                  80

Gly Val Arg Phe His Pro Asp Val Thr Glu Arg Glu Val Lys Ala Leu
                85                  90                  95

Ser Ile Trp Met Ser Leu Lys Cys Gly Ile Val Asp Leu Pro Tyr Gly
            100                 105                 110

Gly Gly Lys Gly Gly Ile Val Cys Asp Pro Arg Thr Met Ser Phe Arg
        115                 120                 125

Glu Leu Glu Arg Leu Ser Arg Gly Tyr Val Arg Ala Ile Ser Gln Ile
    130                 135                 140

Val Gly Pro Thr Lys Asp Ile Pro Ala Pro Asp Val Phe Thr Asn Ser
145                 150                 155                 160

Gln Ile Met Ala Trp Met Met Asp Glu Tyr Ser Arg Ile Arg Glu Phe
                165                 170                 175
```

```
Asp Ser Pro Gly Phe Ile Thr Gly Lys Pro Leu Val Leu Gly Gly Ser
            180                 185                 190

His Gly Arg Glu Thr Ala Thr Ala Lys Gly Val Thr Ile Cys Ile Arg
        195                 200                 205

Glu Ala Ala Lys Lys Arg Gly Leu Ser Leu Glu Gly Ala Arg Val Val
    210                 215                 220

Val Gln Gly Phe Gly Asn Ala Gly Ser Tyr Leu Ala Lys Phe Leu His
225                 230                 235                 240

Asp Ala Gly Ala Lys Val Val Gly Ile Ser Asp Val Tyr Gly Ala Leu
                245                 250                 255

Tyr Asp Pro Asn Gly Leu Asp Ile Asp Tyr Leu Leu Glu Arg Arg Asp
            260                 265                 270

Ser Phe Gly Thr Val Thr Lys Leu Phe Lys Asn Thr Ile Ser Asn Lys
        275                 280                 285

Glu Leu Leu Glu Leu Asp Cys Asp Ile Leu Val Pro Ala Ala Ile Glu
    290                 295                 300

Asn Gln Ile Thr Ala Glu Asn Ala Pro Arg Ile Lys Ala Ser Ile Val
305                 310                 315                 320

Val Glu Ala Ala Asn Gly Pro Thr Thr Leu Glu Ala Thr Glu Ile Leu
                325                 330                 335

Thr Gln Arg Gly Ile Leu Leu Val Pro Asp Val Leu Ala Ser Ala Gly
            340                 345                 350

Gly Ala Thr Val Ser Tyr Phe Glu Trp Val Gln Asn Gln Gly Tyr
        355                 360                 365

Tyr Trp Thr Glu Glu Glu Val Glu Gln Arg Leu Glu Lys Val Met Val
    370                 375                 380

Lys Ala Phe Asn Asn Val Tyr Glu Met Ala Gln Thr Arg Arg Val Asp
385                 390                 395                 400

Met Arg Leu Ala Ala Tyr Met Val Gly Val Arg Lys Met Ala Glu Ala
                405                 410                 415

Cys Arg Phe Arg Gly Trp Val
            420

<210> SEQ ID NO 11
<211> LENGTH: 424
<212> TYPE: PRT
<213> ORGANISM: Artificial
<220> FEATURE:
<223> OTHER INFORMATION: Bacillus subtilis glutamate dehydrogenase
      mutant

<400> SEQUENCE: 11

Met Ser Ala Lys Gln Val Ser Lys Asp Glu Glu Lys Glu Ala Leu Asn
1               5                   10                  15

Leu Phe Leu Ser Thr Gln Thr Ile Ile Lys Glu Ala Leu Arg Lys Leu
                20                  25                  30

Gly Tyr Pro Gly Asp Met Tyr Glu Leu Met Lys Glu Pro Gln Arg Met
            35                  40                  45

Leu Thr Val Arg Ile Pro Val Lys Met Asp Asn Gly Ser Val Lys Val
        50                  55                  60

Phe Thr Gly Tyr Arg Ser Gln His Asn Asp Ala Val Gly Pro Thr Lys
65                  70                  75                  80

Gly Gly Val Arg Phe His Pro Glu Val Asn Glu Glu Val Lys Ala
                85                  90                  95

Leu Ser Ile Trp Met Thr Leu Lys Cys Gly Ile Ala Asn Leu Pro Tyr
            100                 105                 110
```

```
Gly Gly Gly Lys Gly Gly Ile Ile Cys Asp Pro Arg Thr Met Ser Phe
            115                 120                 125

Gly Glu Leu Glu Arg Leu Ser Arg Gly Tyr Val Arg Ala Ile Ser Gln
        130                 135                 140

Ile Val Gly Pro Thr Lys Asp Ile Pro Gly Pro Asp Val Tyr Thr Asn
145                 150                 155                 160

Ser Gln Ile Met Ala Trp Met Met Asp Glu Tyr Ser Arg Leu Arg Glu
                165                 170                 175

Phe Asp Ser Pro Gly Phe Ile Thr Gly Lys Pro Leu Val Leu Gly Gly
            180                 185                 190

Ser Gln Gly Arg Glu Thr Ala Thr Ala Gln Gly Val Thr Ile Cys Ile
        195                 200                 205

Glu Glu Ala Val Lys Lys Lys Gly Ile Lys Leu Gln Asn Ala Arg Ile
    210                 215                 220

Ile Ile Gln Gly Phe Gly Asn Ala Gly Ser Phe Leu Ala Lys Phe Met
225                 230                 235                 240

His Asp Ala Gly Ala Lys Val Ile Gly Ile Ser Asp Ala Asn Gly Gly
                245                 250                 255

Leu Tyr Asn Pro Asp Gly Leu Asp Ile Pro Tyr Leu Leu Asp Lys Arg
            260                 265                 270

Asp Ser Phe Gly Met Val Thr Asn Leu Phe Thr Asp Val Ile Thr Asn
        275                 280                 285

Glu Glu Leu Leu Glu Lys Asp Cys Asp Ile Leu Val Pro Ala Ala Ile
    290                 295                 300

Ser Asn Gln Ile Thr Ala Lys Asn Ala His Asn Ile Gln Ala Ser Ile
305                 310                 315                 320

Val Val Glu Ala Ala Asn Gly Pro Thr Thr Ile Asp Ala Thr Lys Ile
                325                 330                 335

Leu Asn Glu Arg Gly Val Leu Leu Val Pro Asp Ile Leu Ala Ser Ala
            340                 345                 350

Gly Gly Val Thr Val Ser Tyr Phe Glu Trp Val Gln Asn Asn Gln Gly
        355                 360                 365

Tyr Tyr Trp Ser Glu Glu Val Ala Glu Lys Leu Arg Ser Val Met
    370                 375                 380

Val Ser Ser Phe Glu Thr Ile Tyr Gln Thr Ala Ala Thr His Lys Val
385                 390                 395                 400

Asp Met Arg Leu Ala Ala Tyr Met Thr Gly Ile Arg Lys Ser Ala Glu
                405                 410                 415

Ala Ser Arg Phe Arg Gly Trp Val
            420
```

<210> SEQ ID NO 12
<211> LENGTH: 424
<212> TYPE: PRT
<213> ORGANISM: Artificial
<220> FEATURE:
<223> OTHER INFORMATION: Bacillus subtilis glutamate dehydrogenase
      mutant

<400> SEQUENCE: 12

```
Met Ser Ala Lys Gln Val Ser Lys Asp Glu Glu Lys Glu Ala Leu Asn
1               5                   10                  15

Leu Phe Leu Ser Thr Gln Thr Ile Ile Lys Glu Ala Leu Arg Lys Leu
            20                  25                  30

Gly Tyr Pro Gly Asp Met Tyr Glu Leu Met Lys Glu Pro Gln Arg Met
```

```
                35                  40                  45
Leu Thr Val Arg Ile Pro Val Lys Met Asp Asn Gly Ser Val Lys Val
 50                  55                  60

Phe Thr Gly Tyr Arg Ser Gln His Asn Asp Ala Val Gly Pro Thr Lys
 65                  70                  75                  80

Gly Gly Val Arg Phe His Pro Glu Val Asn Glu Glu Val Lys Ala
                 85                  90                  95

Leu Ser Ile Trp Met Thr Leu Lys Cys Gly Ile Ala Asn Leu Pro Tyr
                100                 105                 110

Gly Gly Gly Lys Gly Gly Ile Ile Cys Asp Pro Arg Thr Met Ser Phe
            115                 120                 125

Gly Glu Leu Glu Arg Leu Ser Arg Gly Tyr Val Arg Ala Ile Ser Gln
        130                 135                 140

Ile Val Gly Pro Thr Lys Asp Ile Pro Ala Pro Asp Val Tyr Thr Asn
145                 150                 155                 160

Ser Gln Ile Met Ala Trp Met Met Asp Glu Tyr Ser Arg Leu Arg Glu
                165                 170                 175

Phe Asp Ser Pro Gly Phe Ile Thr Gly Lys Pro Leu Val Leu Gly Gly
            180                 185                 190

Ser Gln Gly Arg Glu Thr Ala Thr Ala Gln Gly Val Thr Ile Cys Ile
        195                 200                 205

Glu Glu Ala Val Lys Lys Gly Ile Lys Leu Gln Asn Ala Arg Ile
210                 215                 220

Ile Ile Gln Gly Phe Gly Asn Ala Gly Ser Phe Leu Ala Lys Phe Met
225                 230                 235                 240

His Asp Ala Gly Ala Lys Val Ile Gly Ile Ser Asp Ala Asn Gly Gly
                245                 250                 255

Leu Tyr Asn Pro Asp Gly Leu Asp Ile Pro Tyr Leu Leu Asp Lys Arg
            260                 265                 270

Asp Ser Phe Gly Met Val Thr Asn Leu Phe Thr Asp Val Ile Thr Asn
        275                 280                 285

Glu Glu Leu Leu Glu Lys Asp Cys Asp Ile Leu Val Pro Ala Ala Ile
        290                 295                 300

Ser Asn Gln Ile Thr Ala Lys Asn Ala His Asn Ile Gln Ala Ser Ile
305                 310                 315                 320

Val Val Glu Ala Ala Asn Gly Pro Thr Thr Ile Asp Ala Thr Lys Ile
                325                 330                 335

Leu Asn Glu Arg Gly Val Leu Leu Val Pro Asp Ile Leu Ala Ser Ala
            340                 345                 350

Gly Gly Ala Thr Val Ser Tyr Phe Glu Trp Val Gln Asn Asn Gln Gly
        355                 360                 365

Tyr Tyr Trp Ser Glu Glu Val Ala Glu Lys Leu Arg Ser Val Met
        370                 375                 380

Val Ser Ser Phe Glu Thr Ile Tyr Gln Thr Ala Ala Thr His Lys Val
385                 390                 395                 400

Asp Met Arg Leu Ala Ala Tyr Met Thr Gly Ile Arg Lys Ser Ala Glu
            405                 410                 415

Ala Ser Arg Phe Arg Gly Trp Val
            420
```

<210> SEQ ID NO 13
<211> LENGTH: 426
<212> TYPE: PRT
<213> ORGANISM: Artificial

<220> FEATURE:
<223> OTHER INFORMATION: Bacillus megaterium glutamate dehydrogenase
      mutant

<400> SEQUENCE: 13

```
Met Val Ala Asp Lys Met Gln Asp Ser Lys Asn Ser Gln Glu Glu Lys
1               5                   10                  15

His Asp Val Leu Lys Ser Thr Gln Thr Val Ile His Lys Ala Leu Glu
            20                  25                  30

Lys Leu Gly Tyr Pro Asp Glu Val Tyr Glu Leu Leu Lys Glu Pro Leu
        35                  40                  45

Arg Met Met Thr Val Lys Ile Pro Val Arg Met Asp Asp Gly Ser Val
50                  55                  60

Lys Ile Phe Thr Gly His Arg Ala Gln His Asn Asp Ala Val Gly Pro
65                  70                  75                  80

Thr Lys Gly Gly Ile Arg Phe His Pro Asn Val Thr Glu Lys Glu Val
                85                  90                  95

Lys Ala Leu Ser Ile Trp Met Ser Leu Lys Cys Gly Ile Val Asp Leu
            100                 105                 110

Pro Tyr Gly Gly Gly Lys Gly Gly Ile Val Cys Asp Pro Arg Asn Met
        115                 120                 125

Ser Phe Gly Glu Leu Glu Arg Leu Ser Arg Gly Tyr Val Arg Ala Ile
130                 135                 140

Ser Gln Ile Val Gly Pro Thr Lys Asp Ile Pro Gly Pro Asp Val Phe
145                 150                 155                 160

Thr Asn Ser Gln Ile Met Ala Trp Met Met Asp Glu Tyr Ser Arg Ile
                165                 170                 175

Asp Glu Phe Asn Ser Pro Gly Phe Ile Thr Gly Lys Pro Leu Val Leu
            180                 185                 190

Gly Gly Ser His Gly Arg Glu Thr Ala Thr Ala Lys Gly Val Thr Ile
        195                 200                 205

Cys Ile Arg Glu Ala Ala Lys Lys Arg Gly Ile Glu Leu Gln Gly Ala
210                 215                 220

Arg Val Val Val Gln Gly Phe Gly Asn Ala Gly Ser Phe Leu Ala Lys
225                 230                 235                 240

Phe Met His Asp Ala Gly Ala Lys Ile Val Gly Ile Ser Asp Ala Tyr
                245                 250                 255

Gly Ala Leu His Asp Pro Asn Gly Leu Asp Ile Asp Tyr Leu Leu Asp
            260                 265                 270

Arg Arg Asp Ser Phe Gly Thr Val Thr Lys Leu Phe Asn Asn Thr Ile
        275                 280                 285

Ser Asn Lys Glu Leu Leu Glu Leu Asp Cys Asp Ile Leu Val Pro Ala
290                 295                 300

Ala Ile Glu Asn Gln Ile Thr Glu Glu Asn Ala His Asn Ile Gln Ala
305                 310                 315                 320

Ser Ile Val Val Glu Ala Ala Asn Gly Pro Thr Thr Leu Glu Ala Thr
                325                 330                 335

Arg Ile Leu Ser Glu Arg Gly Ile Leu Leu Val Pro Asp Val Leu Ala
            340                 345                 350

Ser Ala Gly Gly Val Thr Val Ser Tyr Phe Glu Trp Val Gln Asn Asn
        355                 360                 365

Gln Gly Tyr Tyr Trp Thr Glu Glu Val Glu Glu Lys Leu Glu Lys
370                 375                 380

Val Met Val Lys Ser Phe Asn Asn Ile Tyr Glu Thr Ser Thr Thr Arg
```

Lys Val Asp Met Arg Leu Ala Ala Tyr Met Ile Gly Val Arg Lys Met
385                 390                 395                 400
Ala Glu Gly Ser Arg Phe Arg Gly Trp Ile
            405                 410                 415

420                 425

<210> SEQ ID NO 14
<211> LENGTH: 426
<212> TYPE: PRT
<213> ORGANISM: Artificial
<220> FEATURE:
<223> OTHER INFORMATION: Bacillus megaterium glutamate dehydrogenase
      mutant

<400> SEQUENCE: 14

Met Val Ala Asp Lys Met Gln Asp Ser Lys Asn Ser Gln Glu Glu Lys
1               5                   10                  15
His Asp Val Leu Lys Ser Thr Gln Thr Val Ile His Lys Ala Leu Glu
            20                  25                  30
Lys Leu Gly Tyr Pro Asp Glu Val Tyr Glu Leu Leu Lys Glu Pro Leu
        35                  40                  45
Arg Met Met Thr Val Lys Ile Pro Val Arg Met Asp Asp Gly Ser Val
    50                  55                  60
Lys Ile Phe Thr Gly His Arg Ala Gln His Asn Asp Ala Val Gly Pro
65                  70                  75                  80
Thr Lys Gly Gly Ile Arg Phe His Pro Asn Val Thr Glu Lys Glu Val
            85                  90                  95
Lys Ala Leu Ser Ile Trp Met Ser Leu Lys Cys Gly Ile Val Asp Leu
        100                 105                 110
Pro Tyr Gly Gly Gly Lys Gly Gly Ile Val Cys Asp Pro Arg Asn Met
    115                 120                 125
Ser Phe Gly Glu Leu Glu Arg Leu Ser Arg Gly Tyr Val Arg Ala Ile
130                 135                 140
Ser Gln Ile Val Gly Pro Thr Lys Asp Ile Pro Ala Pro Asp Val Phe
145                 150                 155                 160
Thr Asn Ser Gln Ile Met Ala Trp Met Met Asp Glu Tyr Ser Arg Ile
            165                 170                 175
Asp Glu Phe Asn Ser Pro Gly Phe Ile Thr Gly Lys Pro Leu Val Leu
        180                 185                 190
Gly Gly Ser His Gly Arg Glu Thr Ala Thr Ala Lys Gly Val Thr Ile
    195                 200                 205
Cys Ile Arg Glu Ala Ala Lys Lys Arg Gly Ile Glu Leu Gln Gly Ala
210                 215                 220
Arg Val Val Gln Gly Phe Gly Asn Ala Gly Ser Phe Leu Ala Lys
225                 230                 235                 240
Phe Met His Asp Ala Gly Ala Lys Ile Val Gly Ile Ser Asp Ala Tyr
            245                 250                 255
Gly Ala Leu His Asp Pro Asn Gly Leu Asp Ile Asp Tyr Leu Leu Asp
        260                 265                 270
Arg Arg Asp Ser Phe Gly Thr Val Thr Lys Leu Phe Asn Asn Thr Ile
    275                 280                 285
Ser Asn Lys Glu Leu Leu Glu Leu Asp Cys Asp Ile Leu Val Pro Ala
290                 295                 300
Ala Ile Glu Asn Gln Ile Thr Glu Glu Asn Ala His Asn Ile Gln Ala
305                 310                 315                 320

-continued

```
Ser Ile Val Val Glu Ala Ala Asn Gly Pro Thr Thr Leu Glu Ala Thr
                325                 330                 335

Arg Ile Leu Ser Glu Arg Gly Ile Leu Leu Val Pro Asp Val Leu Ala
            340                 345                 350

Ser Ala Gly Gly Ala Thr Val Ser Tyr Phe Glu Trp Val Gln Asn Asn
        355                 360                 365

Gln Gly Tyr Tyr Trp Thr Glu Glu Val Glu Lys Leu Glu Lys
    370                 375                 380

Val Met Val Lys Ser Phe Asn Asn Ile Tyr Glu Thr Ser Thr Thr Arg
385                 390                 395                 400

Lys Val Asp Met Arg Leu Ala Ala Tyr Met Ile Gly Val Arg Lys Met
                405                 410                 415

Ala Glu Gly Ser Arg Phe Arg Gly Trp Ile
            420                 425

<210> SEQ ID NO 15
<211> LENGTH: 414
<212> TYPE: PRT
<213> ORGANISM: Artificial
<220> FEATURE:
<223> OTHER INFORMATION: Lysinibacillus sphaericus glutamate
      dehydrogenase mutant

<400> SEQUENCE: 15

Met Ser Glu Asn Leu Asn Leu Phe Thr Ser Thr Gln Asp Val Ile Gln
1               5                   10                  15

Asp Ala Leu Asn Lys Leu Gly Tyr Asp Glu Ala Met Tyr Glu Leu Leu
            20                  25                  30

Lys Glu Pro Leu Arg Met Leu Gln Val Arg Ile Pro Val Lys Met Asp
        35                  40                  45

Asp Gly Thr Thr Lys Val Phe Thr Gly Tyr Arg Ala Gln His Asn Asp
    50                  55                  60

Ala Val Gly Pro Thr Lys Gly Val Arg Phe His Pro Gln Val Ser
65                  70                  75                  80

Glu Glu Glu Val Lys Ala Leu Ser Met Trp Met Thr Leu Lys Cys Gly
                85                  90                  95

Ile Val Asp Leu Pro Tyr Gly Gly Lys Gly Gly Val Ile Cys Asp
            100                 105                 110

Pro Arg Gln Met Ser Met Gly Glu Ile Glu Arg Leu Ser Arg Gly Tyr
        115                 120                 125

Val Arg Ala Val Ser Gln Ile Val Gly Pro Thr Lys Asp Ile Pro Gly
    130                 135                 140

Pro Asp Val Phe Thr Asn Ala Gln Ile Met Ala Trp Met Met Asp Glu
145                 150                 155                 160

Tyr Ser Arg Met Asp Glu Phe Asn Ser Pro Gly Phe Ile Thr Gly Lys
                165                 170                 175

Pro Leu Val Leu Gly Gly Ser Gln Gly Arg Asp Arg Ala Thr Ala Gln
            180                 185                 190

Gly Val Thr Ile Val Glu Glu Ala Ala Lys Lys Arg Gly Ile Asp
        195                 200                 205

Ile Lys Gly Ala Arg Val Val Ile Gln Gly Phe Gly Asn Ala Gly Ser
    210                 215                 220

Phe Leu Ala Lys Phe Met His Asp Leu Gly Ala Lys Val Ile Gly Ile
225                 230                 235                 240

Ser Asp Ala Tyr Gly Ala Leu His Asp Pro Glu Gly Leu Asp Ile Asp
                245                 250                 255
```

Tyr Leu Leu Asp Arg Arg Asp Ser Phe Gly Thr Val Thr Thr Leu Phe
                260                 265                 270

Glu Asn Thr Ile Ser Asn Lys Glu Leu Glu Leu Asp Cys Asp Ile
            275                 280                 285

Leu Val Pro Ala Ala Ile Glu Asn Gln Ile Thr Ala Asp Asn Ala His
290                 295                 300

Asn Ile Lys Ala Asp Ile Val Val Glu Ala Ala Asn Gly Pro Thr Thr
305                 310                 315                 320

Ala Glu Ala Thr Lys Ile Leu Thr Glu Arg Gly Ile Leu Leu Val Pro
                325                 330                 335

Asp Val Leu Ala Ser Ala Gly Gly Val Thr Val Ser Tyr Phe Glu Trp
            340                 345                 350

Val Gln Asn Asn Gln Gly Tyr Tyr Trp Thr Glu Glu Val Glu Glu
        355                 360                 365

Arg Leu Tyr Lys Lys Met Val Glu Ala Phe Asp Asn Val Tyr Thr Thr
370                 375                 380

Ala Thr Thr Arg Asn Ile Asn Met Arg Leu Ala Ala Tyr Met Val Gly
385                 390                 395                 400

Val Arg Arg Thr Ala Glu Ala Ser Arg Phe Arg Gly Trp Val
                405                 410

<210> SEQ ID NO 16
<211> LENGTH: 414
<212> TYPE: PRT
<213> ORGANISM: Artificial
<220> FEATURE:
<223> OTHER INFORMATION: Lysinibacillus sphaericus glutamate
      dehydrogenase mutant

<400> SEQUENCE: 16

Met Ser Glu Asn Leu Asn Leu Phe Thr Ser Thr Gln Asp Val Ile Gln
1               5                   10                  15

Asp Ala Leu Asn Lys Leu Gly Tyr Asp Glu Ala Met Tyr Glu Leu Leu
            20                  25                  30

Lys Glu Pro Leu Arg Met Leu Gln Val Arg Ile Pro Val Lys Met Asp
        35                  40                  45

Asp Gly Thr Thr Lys Val Phe Thr Gly Tyr Arg Ala Gln His As

```
                195                 200                 205
Ile Lys Gly Ala Arg Val Val Ile Gln Gly Phe Gly Asn Ala Gly Ser
210                 215                 220
Phe Leu Ala Lys Phe Met His Asp Leu Gly Ala Lys Val Ile Gly Ile
225                 230                 235                 240
Ser Asp Ala Tyr Gly Ala Leu His Asp Pro Glu Gly Leu Asp Ile Asp
                245                 250                 255
Tyr Leu Leu Asp Arg Arg Asp Ser Phe Gly Thr Val Thr Thr Leu Phe
                260                 265                 270
Glu Asn Thr Ile Ser Asn Lys Glu Leu Leu Glu Leu Asp Cys Asp Ile
                275                 280                 285
Leu Val Pro Ala Ala Ile Glu Asn Gln Ile Thr Ala Asp Asn Ala His
                290                 295                 300
Asn Ile Lys Ala Asp Ile Val Glu Ala Ala Asn Gly Pro Thr Thr
305                 310                 315                 320
Ala Glu Ala Thr Lys Ile Leu Thr Glu Arg Gly Ile Leu Leu Val Pro
                325                 330                 335
Asp Val Leu Ala Ser Ala Gly Gly Ala Thr Val Ser Tyr Phe Glu Trp
                340                 345                 350
Val Gln Asn Asn Gln Gly Tyr Tyr Trp Thr Glu Glu Val Glu Glu
                355                 360                 365
Arg Leu Tyr Lys Lys Met Val Glu Ala Phe Asp Asn Val Tyr Thr Thr
370                 375                 380
Ala Thr Thr Arg Asn Ile Asn Met Arg Leu Ala Ala Tyr Met Val Gly
385                 390                 395                 400
Val Arg Arg Thr Ala Glu Ala Ser Arg Phe Arg Gly Trp Val
                405                 410

<210> SEQ ID NO 17
<211> LENGTH: 450
<212> TYPE: PRT
<213> ORGANISM: Artificial
<220> FEATURE:
<223> OTHER INFORMATION: Clostridium symbiosum glutamate dehydrogenase
      mutant

<400> SEQUENCE: 17

Met Ser Lys Tyr Val Asp Arg Val Ile Ala Glu Val Glu Lys Lys Tyr
1               5                   10                  15
Ala Asp Glu Pro Glu Phe Val Gln Thr Val Glu Glu Val Leu Ser Ser
                20                  25                  30
Leu Gly Pro Val Val Asp Ala His Pro Glu Tyr Glu Glu Val Ala Leu
                35                  40                  45
Leu Glu Arg Met Val Ile Pro Glu Arg Val Ile Glu Phe Arg Val Pro
        50                  55                  60
Trp Glu Asp Asp Asn Gly Lys Val His Val Asn Thr Gly Tyr Arg Val
65              70                  75                  80
Gln Phe Asn Gly Ala Ile Gly Pro Tyr Lys Gly Gly Leu Arg Phe Ala
                85                  90                  95
Pro Ser Val Asn Leu Ser Ile Met Lys Phe Leu Gly Phe Glu Gln Ala
                100                 105                 110
Phe Lys Asp Ser Leu Thr Thr Leu Pro Met Gly Gly Ala Lys Gly Gly
                115                 120                 125
Ser Asp Phe Asp Pro Asn Gly Lys Ser Asp Arg Glu Val Met Arg Phe
        130                 135                 140
```

```
Cys Gln Ala Phe Met Thr Glu Leu Tyr Arg His Ile Gly Pro Asp Ile
145                 150                 155                 160

Asp Val Pro Gly Gly Asp Leu Gly Val Gly Ala Arg Glu Ile Gly Tyr
            165                 170                 175

Met Tyr Gly Gln Tyr Arg Lys Ile Val Gly Gly Phe Tyr Asn Gly Val
            180                 185                 190

Leu Thr Gly Lys Ala Arg Ser Phe Gly Gly Ser Leu Val Arg Pro Glu
            195                 200                 205

Ala Thr Gly Tyr Gly Ser Val Tyr Tyr Val Glu Ala Val Met Lys His
            210                 215                 220

Glu Asn Asp Thr Leu Val Gly Lys Thr Val Ala Leu Ala Gly Phe Gly
225                 230                 235                 240

Asn Val Ala Trp Gly Ala Ala Lys Lys Leu Ala Glu Leu Gly Ala Lys
                245                 250                 255

Ala Val Thr Leu Ser Gly Pro Asp Gly Tyr Ile Tyr Asp Pro Glu Gly
            260                 265                 270

Ile Thr Thr Glu Glu Lys Ile Asn Tyr Met Leu Glu Met Arg Ala Ser
            275                 280                 285

Gly Arg Asn Lys Val Gln Asp Tyr Ala Asp Lys Phe Gly Val Gln Phe
            290                 295                 300

Phe Pro Gly Glu Lys Pro Trp Gly Gln Lys Val Asp Ile Ile Met Pro
305                 310                 315                 320

Cys Ala Thr Gln Asn Asp Val Asp Leu Glu Gln Ala Lys Lys Ile Val
                325                 330                 335

Ala Asn Asn Ile Lys Tyr Tyr Ile Glu Val Ala Asn Met Pro Thr Thr
            340                 345                 350

Asn Glu Ala Leu Arg Phe Leu Met Gln Gln Pro Asn Met Val Val Ala
            355                 360                 365

Pro Ser Lys Ala Val Asn Ala Gly Gly Val Leu Val Ser Gly Phe Glu
            370                 375                 380

Met Ser Gln Asn Ser Glu Arg Leu Ser Trp Thr Ala Glu Glu Val Asp
385                 390                 395                 400

Ser Lys Leu His Gln Val Met Thr Asp Ile His Asp Gly Ser Ala Ala
                405                 410                 415

Ala Ala Glu Arg Tyr Gly Leu Gly Tyr Asn Leu Val Ala Gly Ala Asn
            420                 425                 430

Ile Val Gly Phe Gln Lys Ile Ala Asp Ala Met Met Ala Gln Gly Ile
            435                 440                 445

Ala Trp
450

<210> SEQ ID NO 18
<211> LENGTH: 450
<212> TYPE: PRT
<213> ORGANISM: Artificial
<220> FEATURE:
<223> OTHER INFORMATION: Clostridium symbiosum glutamate dehydrogenase
      mutant

<400> SEQUENCE: 18

Met Ser Lys Tyr Val Asp Arg Val Ile Ala Glu Val Glu Lys Lys Tyr
1               5                   10                  15

Ala Asp Glu Pro Glu Phe Val Gln Thr Val Glu Glu Val Leu Ser Ser
            20                  25                  30

Leu Gly Pro Val Val Asp Ala His Pro Glu Tyr Glu Glu Val Ala Leu
            35                  40                  45
```

```
Leu Glu Arg Met Val Ile Pro Glu Arg Val Ile Glu Phe Arg Val Pro
 50                  55                  60

Trp Glu Asp Asp Asn Gly Lys Val His Val Asn Thr Gly Tyr Arg Val
 65                  70                  75                  80

Gln Phe Asn Gly Ala Ile Gly Pro Tyr Lys Gly Gly Leu Arg Phe Ala
                 85                  90                  95

Pro Ser Val Asn Leu Ser Ile Met Lys Phe Leu Gly Phe Glu Gln Ala
                100                 105                 110

Phe Lys Asp Ser Leu Thr Thr Leu Pro Met Gly Gly Ala Lys Gly Gly
            115                 120                 125

Ser Asp Phe Asp Pro Asn Gly Lys Ser Asp Arg Glu Val Met Arg Phe
130                 135                 140

Cys Gln Ala Phe Met Thr Glu Leu Tyr Arg His Ile Gly Pro Asp Ile
145                 150                 155                 160

Asp Val Pro Ala Gly Asp Leu Gly Val Gly Ala Arg Glu Ile Gly Tyr
                165                 170                 175

Met Tyr Gly Gln Tyr Arg Lys Ile Val Gly Gly Phe Tyr Asn Gly Val
            180                 185                 190

Leu Thr Gly Lys Ala Arg Ser Phe Gly Gly Ser Leu Val Arg Pro Glu
            195                 200                 205

Ala Thr Gly Tyr Gly Ser Val Tyr Tyr Val Glu Ala Val Met Lys His
            210                 215                 220

Glu Asn Asp Thr Leu Val Gly Lys Thr Val Ala Leu Ala Gly Phe Gly
225                 230                 235                 240

Asn Val Ala Trp Gly Ala Ala Lys Lys Leu Ala Glu Leu Gly Ala Lys
                245                 250                 255

Ala Val Thr Leu Ser Gly Pro Asp Gly Tyr Ile Tyr Asp Pro Glu Gly
            260                 265                 270

Ile Thr Thr Glu Glu Lys Ile Asn Tyr Met Leu Glu Met Arg Ala Ser
            275                 280                 285

Gly Arg Asn Lys Val Gln Asp Tyr Ala Asp Lys Phe Gly Val Gln Phe
            290                 295                 300

Phe Pro Gly Glu Lys Pro Trp Gly Gln Lys Val Asp Ile Ile Met Pro
305                 310                 315                 320

Cys Ala Thr Gln Asn Asp Val Asp Leu Glu Gln Ala Lys Lys Ile Val
                325                 330                 335

Ala Asn Asn Ile Lys Tyr Tyr Ile Glu Val Ala Asn Met Pro Thr Thr
                340                 345                 350

Asn Glu Ala Leu Arg Phe Leu Met Gln Gln Pro Asn Met Val Val Ala
                355                 360                 365

Pro Ser Lys Ala Val Asn Ala Gly Gly Ala Leu Val Ser Gly Phe Glu
            370                 375                 380

Met Ser Gln Asn Ser Glu Arg Leu Ser Trp Thr Ala Glu Glu Val Asp
385                 390                 395                 400

Ser Lys Leu His Gln Val Met Thr Asp Ile His Asp Gly Ser Ala Ala
                405                 410                 415

Ala Ala Glu Arg Tyr Gly Leu Gly Tyr Asn Leu Val Ala Gly Ala Asn
            420                 425                 430

Ile Val Gly Phe Gln Lys Ile Ala Asp Ala Met Met Ala Gln Gly Ile
            435                 440                 445

Ala Trp
450
```

<210> SEQ ID NO 19
<211> LENGTH: 425
<212> TYPE: PRT
<213> ORGANISM: Artificial
<220> FEATURE:
<223> OTHER INFORMATION: Brevibacillus thermoruber glutamate
      dehydrogenase mutant

<400> SEQUENCE: 19

| Met | Val | Thr | Glu | Asn | Thr | Gln | Gly | Lys | Glu | Gln | Lys | Gln | Ser | Met |
| 1 | | | | 5 | | | | | 10 | | | | | 15 |

| Asn | Leu | Leu | Gln | Ser | Thr | Gln | Thr | Val | Ile | Lys | Glu | Ala | Leu | Glu | Lys |
| | | | 20 | | | | | 25 | | | | | 30 | | |

| Leu | Gly | Tyr | Gln | Glu | Ser | Met | Tyr | Glu | Leu | Leu | Lys | Glu | Pro | Leu | Arg |
| | | 35 | | | | | 40 | | | | | 45 | | | |

| Val | Leu | Thr | Val | Arg | Ile | Pro | Val | Arg | Met | Asp | Asn | Gly | Glu | Val | Lys |
| 50 | | | | | 55 | | | | | 60 | | | | | |

| Val | Phe | Thr | Gly | Tyr | Arg | Ala | Gln | His | Asn | Asp | Ala | Val | Gly | Pro | Thr |
| 65 | | | | | 70 | | | | | 75 | | | | | 80 |

| Lys | Gly | Gly | Ile | Arg | Phe | His | Pro | Asp | Val | Thr | Glu | Asp | Glu | Val | Lys |
| | | | | 85 | | | | | 90 | | | | | 95 | |

| Ala | Leu | Ser | Ile | Trp | Met | Ser | Leu | Lys | Ala | Gly | Ile | Val | Asp | Leu | Pro |
| | | | 100 | | | | | 105 | | | | | 110 | | |

| Tyr | Gly | Gly | Gly | Lys | Gly | Gly | Ile | Ile | Cys | Asp | Pro | Arg | Glu | Met | Ser |
| | | 115 | | | | | 120 | | | | | 125 | | | |

| Phe | Arg | Glu | Leu | Glu | Arg | Leu | Ser | Arg | Gly | Tyr | Val | Arg | Ala | Val | Ser |
| 130 | | | | | 135 | | | | | 140 | | | | | |

| Gln | Ile | Val | Gly | Pro | Thr | Lys | Asp | Ile | Pro | Gly | Pro | Asp | Val | Phe | Thr |
| 145 | | | | | 150 | | | | | 155 | | | | | 160 |

| Asn | Ser | Gln | Ile | Met | Ala | Trp | Met | Met | Asp | Glu | Tyr | Ser | Arg | Ile | Arg |
| | | | | 165 | | | | | 170 | | | | | 175 | |

| Glu | Phe | Asp | Ser | Pro | Gly | Phe | Ile | Thr | Gly | Lys | Pro | Ile | Ala | Leu | Gly |
| | | | 180 | | | | | 185 | | | | | 190 | | |

| Gly | Ser | His | Gly | Arg | Glu | Thr | Ala | Thr | Ala | Lys | Gly | Val | Thr | Ile | Cys |
| | | 195 | | | | | 200 | | | | | 205 | | | |

| Ile | Arg | Glu | Ala | Ala | Lys | Arg | Arg | Gly | Ile | Asp | Leu | Lys | Gly | Ala | Arg |
| 210 | | | | | 215 | | | | | 220 | | | | | |

| Val | Val | Val | Gln | Gly | Phe | Gly | Asn | Ala | Gly | Ser | Tyr | Leu | Ser | Lys | Phe |
| 225 | | | | | 230 | | | | | 235 | | | | | 240 |

| Met | His | Asp | Ala | Gly | Ala | Lys | Val | Val | Gly | Ile | Ser | Asp | Ala | Tyr | Gly |
| | | | | 245 | | | | | 250 | | | | | 255 | |

| Ala | Leu | Tyr | Asp | Pro | Asn | Gly | Leu | Asp | Ile | Asp | Tyr | Leu | Leu | Asp | Arg |
| | | | 260 | | | | | 265 | | | | | 270 | | |

| Arg | Asp | Ser | Phe | Gly | Thr | Val | Thr | Lys | Leu | Phe | Thr | Asn | Thr | Ile | Thr |
| | | 275 | | | | | 280 | | | | | 285 | | | |

| Asn | Lys | Glu | Leu | Leu | Glu | Leu | Asp | Cys | Asp | Ile | Leu | Val | Pro | Ala | Ala |
| 290 | | | | | 295 | | | | | 300 | | | | | |

| Ile | Glu | Asn | Gln | Ile | Thr | Ala | Ala | Asn | Ala | His | Asn | Ile | Lys | Ala | Lys |
| 305 | | | | | 310 | | | | | 315 | | | | | 320 |

| Ile | Val | Val | Glu | Ala | Ala | Asn | Gly | Pro | Thr | Thr | Leu | Glu | Ala | Thr | Lys |
| | | | | 325 | | | | | 330 | | | | | 335 | |

| Ile | Leu | Thr | Glu | Arg | Gly | Ile | Leu | Leu | Val | Pro | Asp | Val | Leu | Ala | Ser |
| | | | 340 | | | | | 345 | | | | | 350 | | |

| Ala | Gly | Gly | Val | Thr | Val | Ser | Tyr | Phe | Glu | Trp | Val | Gln | Asn | Asn | Gln |
| | | 355 | | | | | 360 | | | | | 365 | | | |

```
Gly Tyr Tyr Trp Ser Glu Glu Val Gln Glu Lys Leu Glu Lys Val
        370             375                 380

Met Val Lys Ala Phe Glu Asn Val Tyr Ser Leu Ala Gln Thr Arg Arg
385                 390                 395                 400

Val Asp Met Arg Leu Ala Ala Tyr Met Val Gly Val Arg Lys Met Ala
                405                 410                 415

Glu Ala Ser Arg Phe Arg Gly Trp Val
            420                 425

<210> SEQ ID NO 20
<211> LENGTH: 425
<212> TYPE: PRT
<213> ORGANISM: Artificial
<220> FEATURE:
<223> OTHER INFORMATION: Brevibacillus thermoruber glutamate
      dehydrogenase mutant

<400> SEQUENCE: 20

Met Val Thr Glu Asn Thr Gln Gly Lys Glu Lys Gln Glu Ser Met
1               5                   10                  15

Asn Leu Leu Gln Ser Thr Gln Thr Val Ile Lys Glu Ala Leu Glu Lys
                20                  25                  30

Leu Gly Tyr Gln Glu Ser Met Tyr Glu Leu Leu Lys Glu Pro Leu Arg
            35                  40                  45

Val Leu Thr Val Arg Ile Pro Val Arg Met Asp Asn Gly Glu Val Lys
50                  55                  60

Val Phe Thr Gly Tyr Arg Ala Gln His Asn Asp Ala Val Gly Pro Thr
65                  70                  75                  80

Lys Gly Gly Ile Arg Phe His Pro Asp Val Thr Glu Asp Glu Val Lys
                85                  90                  95

Ala Leu Ser Ile Trp Met Ser Leu Lys Ala Gly Ile Val Asp Leu Pro
            100                 105                 110

Tyr Gly Gly Gly Lys Gly Gly Ile Ile Cys Asp Pro Arg Glu Met Ser
        115                 120                 125

Phe Arg Glu Leu Glu Arg Leu Ser Arg Gly Tyr Val Arg Ala Val Ser
130                 135                 140

Gln Ile Val Gly Pro Thr Lys Asp Ile Pro Ala Pro Asp Val Phe Thr
145                 150                 155                 160

Asn Ser Gln Ile Met Ala Trp Met Met Asp Glu Tyr Ser Arg Ile Arg
                165                 170                 175

Glu Phe Asp Ser Pro Gly Phe Ile Thr Gly Lys Pro Ile Ala Leu Gly
            180                 185                 190

Gly Ser His Gly Arg Glu Thr Ala Thr Ala Lys Gly Val Thr Ile Cys
        195                 200                 205

Ile Arg Glu Ala Ala Lys Arg Arg Gly Ile Asp Leu Lys Gly Ala Arg
210                 215                 220

Val Val Val Gln Gly Phe Gly Asn Ala Gly Ser Tyr Leu Ser Lys Phe
225                 230                 235                 240

Met His Asp Ala Gly Ala Lys Val Val Gly Ile Ser Asp Ala Tyr Gly
                245                 250                 255

Ala Leu Tyr Asp Pro Asn Gly Leu Asp Ile Asp Tyr Leu Leu Asp Arg
            260                 265                 270

Arg Asp Ser Phe Gly Thr Val Thr Lys Leu Phe Thr Asn Thr Ile Thr
        275                 280                 285

Asn Lys Glu Leu Leu Glu Leu Asp Cys Asp Ile Leu Val Pro Ala Ala
```

```
            290                 295                 300
Ile Glu Asn Gln Ile Thr Ala Asn Ala His Asn Ile Lys Ala Lys
305                 310                 315                 320

Ile Val Val Glu Ala Asn Gly Pro Thr Thr Leu Glu Ala Thr Lys
                325                 330                 335

Ile Leu Thr Glu Arg Gly Ile Leu Val Pro Asp Val Leu Ala Ser
                340                 345                 350

Ala Gly Gly Ala Thr Val Ser Tyr Phe Glu Trp Val Gln Asn Asn Gln
                355                 360                 365

Gly Tyr Tyr Trp Ser Glu Glu Val Gln Glu Lys Leu Glu Lys Val
        370                 375                 380

Met Val Lys Ala Phe Glu Asn Val Tyr Ser Leu Ala Gln Thr Arg Arg
385                 390                 395                 400

Val Asp Met Arg Leu Ala Ala Tyr Met Val Gly Val Arg Lys Met Ala
                405                 410                 415

Glu Ala Ser Arg Phe Arg Gly Trp Val
                420                 425

<210> SEQ ID NO 21
<211> LENGTH: 261
<212> TYPE: PRT
<213> ORGANISM: Artificial
<220> FEATURE:
<223> OTHER INFORMATION: Bacillus subtilis glutamate dehydrogenase
      mutant

<400> SEQUENCE: 21

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
                20                  25                  30

Lys Val Val Ile Asn Tyr Tyr Ser Asn Lys Gln Asp Pro Asn Glu Val
            35                  40                  45

Lys Glu Glu Val Ile Lys Ala Gly Gly Glu Ala Val Val Val Gln Gly
        50                  55                  60

Asp Val Thr Lys Glu Glu Asp Val Lys Asn Ile Val Gln Thr Ala Ile
65                  70                  75                  80

Lys Glu Phe Gly Thr Leu Asp Ile Met Ile Asn Asn Ala Gly Leu Glu
                85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
            115                 120                 125

Lys Tyr Phe Val Glu Asn Asp Ile Lys Gly Asn Val Ile Asn Met Ser
        130                 135                 140

Ser Val His Glu Val Ile Pro Trp Pro Leu Phe Val His Tyr Ala Ala
145                 150                 155                 160

Ser Lys Gly Gly Ile Lys Leu Met Thr Arg Thr Leu Ala Leu Glu Tyr
                165                 170                 175

Ala Pro Lys Gly Ile Arg Val Asn Asn Ile Gly Pro Gly Ala Ile Asn
                180                 185                 190

Thr Pro Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
        210                 215                 220
```

```
Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Leu Tyr Pro Ser Phe
            245                 250                 255

Gln Ala Gly Arg Gly
            260
```

<210> SEQ ID NO 22
<211> LENGTH: 449
<212> TYPE: PRT
<213> ORGANISM: Artificial
<220> FEATURE:
<223> OTHER INFORMATION: Pseudomonas putida glutamate dehydrogenase mutant

<400> SEQUENCE: 22

```
Met Ser Thr Met Ile Glu Ser Val Asp Asn Phe Leu Ala Arg Leu Lys
1               5                   10                  15

Gln Arg Asp Pro Gly Gln Pro Glu Phe His Gln Ala Val Glu Glu Val
            20                  25                  30

Leu Arg Thr Leu Trp Pro Phe Leu Glu Ala Asn Pro His Tyr Leu Gln
        35                  40                  45

Ser Gly Ile Leu Glu Arg Met Val Pro Glu Arg Ala Val Leu Phe
50                  55                  60

Arg Val Ser Trp Val Asp Asp Gln Gly Lys Val Gln Val Asn Arg Gly
65                  70                  75                  80

Tyr Arg Ile Gln Met Ser Ser Ala Ile Gly Pro Tyr Lys Gly Gly Leu
                85                  90                  95

Arg Phe His Pro Ser Val Asn Leu Ser Val Leu Lys Phe Leu Ala Phe
            100                 105                 110

Glu Gln Val Phe Lys Asn Ser Leu Thr Ser Leu Pro Met Gly Gly Gly
        115                 120                 125

Lys Gly Gly Ser Asp Phe Asp Pro Lys Gly Lys Ser Asp Ala Glu Val
130                 135                 140

Met Arg Phe Cys Gln Ala Phe Met Ser Glu Leu Tyr Arg His Ile Gly
145                 150                 155                 160

Ala Asp Cys Asp Val Pro Gly Gly Asp Ile Gly Val Gly Ala Arg Glu
                165                 170                 175

Ile Gly Phe Met Phe Gly Gln Tyr Lys Arg Leu Ala Asn Gln Phe Thr
            180                 185                 190

Ser Val Leu Thr Gly Lys Gly Met Thr Tyr Gly Gly Ser Leu Ile Arg
        195                 200                 205

Pro Glu Ala Thr Gly Tyr Gly Cys Val Tyr Phe Ala Glu Glu Met Leu
210                 215                 220

Lys Arg Gln Asp Lys Arg Ile Asp Gly Arg Arg Val Ala Val Ser Gly
225                 230                 235                 240

Ser Gly Asn Val Ala Gln Tyr Ala Ala Arg Lys Val Met Asp Leu Gly
                245                 250                 255

Gly Lys Val Ile Ser Leu Ser Asp Ser Glu Gly Thr Leu Tyr Ala Glu
            260                 265                 270

Ala Gly Leu Thr Asp Ala Gln Trp Asp Ala Leu Met Glu Leu Lys Asn
        275                 280                 285

Val Lys Arg Gly Arg Ile Ser Glu Leu Ala Gly Gln Phe Gly Leu Glu
290                 295                 300

Phe Arg Lys Gly Gln Thr Pro Trp Ser Leu Pro Cys Asp Ile Ala Leu
305                 310                 315                 320
```

```
Pro Cys Ala Thr Gln Asn Glu Leu Gly Ala Glu Asp Ala Arg Thr Leu
            325                 330                 335

Leu Arg Asn Gly Cys Ile Cys Val Ala Glu Gly Ala Asn Met Pro Thr
        340                 345                 350

Thr Leu Glu Ala Val Asp Ile Phe Leu Asp Ala Gly Ile Leu Tyr Ala
        355                 360                 365

Pro Gly Lys Ala Ser Asn Ala Gly Gly Ala Ala Val Ser Gly Leu Glu
        370                 375                 380

Met Ser Gln Asn Ala Met Arg Leu Leu Trp Thr Ala Gly Glu Val Asp
385                 390                 395                 400

Ser Lys Leu His Asn Ile Met Gln Ser Ile His His Ala Cys Val His
                405                 410                 415

Tyr Gly Glu Glu Ala Asp Gly Arg Ile Asn Tyr Val Lys Gly Ala Asn
            420                 425                 430

Ile Ala Gly Phe Val Lys Val Ala Asp Ala Met Leu Ala Gln Gly Val
        435                 440                 445

Val
```

<210> SEQ ID NO 23
<211> LENGTH: 30
<212> TYPE: DNA
<213> ORGANISM: Artificial sequence
<220> FEATURE:
<223> OTHER INFORMATION: Synthesized Primer A167G-F for Site-directed
      Mutation of PpGluDH

<400> SEQUENCE: 23
acgtaccggg tggtgacatc ggtgtggggg                                     30

<210> SEQ ID NO 24
<211> LENGTH: 30
<212> TYPE: DNA
<213> ORGANISM: Artificial Sequence
<220> FEATURE:
<223> OTHER INFORMATION: Synthesized Primer A167G-R for Site-directed
      Mutation of PpGluDH

<400> SEQUENCE: 24
atgtcaccac ccggtacgtc gcagtcagca                                     30

<210> SEQ ID NO 25
<211> LENGTH: 30
<212> TYPE: DNA
<213> ORGANISM: Artificial Sequence
<220> FEATURE:
<223> OTHER INFORMATION: Synthesized Primer V378A-F for Site-directed
      Mutation of PpGluDH

<400> SEQUENCE: 25
cgggcggcgc agccgtgtcg ggcctggaaa                                     30

<210> SEQ ID NO 26
<211> LENGTH: 30
<212> TYPE: DNA
<213> ORGANISM: Artificial Sequence
<220> FEATURE:
<223> OTHER INFORMATION: Synthesized Primer V378A-R for Site-directed
      Mutation of PpGluDH

<400> SEQUENCE: 26
gacacggctg cgccgcccgc attggaggcc                                     30

GLUTAMATE DEHYDROGENASE MUTANTS AND THEIR APPLICATION IN PREPARATION OF L-PHOSPHINOTHRICIN

CROSS-REFERENCE TO RELATED APPLICATION

This application is a 371 application of International PCT application serial no. PCT/CN2018/105158, filed on Sep. 12, 2018, which claims the priority benefit of Chinese application no. 201810194742.0, filed on Mar. 9, 2018. The entirety of each of the abovementioned patent applications is hereby incorporated by reference herein and made a part of this specification.

BACKGROUND

Technical Field

The present invention is related to enzyme engineering field, in particular to glutamate dehydrogenase mutants and their application in preparation of L-phosphinothricin.

Description of Related Art

Phosphinothricin (4-(hydroxymethylphosphinyl)butyric acid) is a phosphor contained amino acid herbicides, of which action target is glutamine synthetase; it features in high activity, excellent absorption, extensive herbicidal spectrum, low toxicity and good environmental compatibility. As No. 3 non-selective herbicide and No. 2 herbicide for genetically modified crops in the world, phosphinothricin has potential for huge market share growth with the development and promotion of genetically modified phosphinothricin-tolerant crops and the shrinking of the market for its main competitor products (glyphosate and paraquat).

In the two enantiomers of phosphinothricin, only L-enantiomer has herbicidal activity; whereas phosphinothricin available in the market is merely its racemate (Herbicidal compositions [P]. Patent application U.S. Pat. No. 4,265,654 A, 1981). Use of L-phosphinothricin monomer can significantly reduce the use quantity of phosphinothricin alleviate environmental pressure and simultaneously reduce the production of weed resistance, which has superior advantages over environmental protection.

Therefore, development of L-phosphinothricin preparation technique has extremely high significance. At laboratory scale, numerous enzyme based L-phosphinothricin preparation peocess have been developed; wherein, a process with certain potential is to use glutamate dehydrogenase for reductive amination of 2-oxo-4-[hydroxy)(methyl)phosphinoyl]butyric acid (PPO) to prepare L-phosphinothricin (Progresses in Biosynthesis of L-Phosphinothricin [J], Modern Agrochemicals, 2009, 8(3): 1-4.).

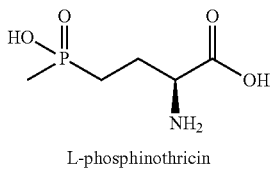

L-phosphinothricin

Glutamate dehydrogenases (EC 1.4.1.2-1.4.1.4) are kind of oxidoreductases that can catalyze the reversible oxidative deamination of L-glutamate to a-ketoglutarate; they are ubiquitous enzymes that exist in nearly all organisms. According to its coenzyme specificity, it can be divided into NADH-specific, NADPH-specific and NADH/NADPH dual coenzyme-specific. Microorganisms generally express a single glutamate dehydrogenase, and they can be either NADH or NADPH-specific; plants express separate NADH and NADPH-specific glutamate dehydrogenases which are compartmentalized into their mitochondria and chloroplasts; whereas dual coenzyme-specific glutamate dehydrogenases are expressed in animal cells (The biochemistry and enzymology of amino acid dehydrogenases[J]. Critical reviews in biochemistry and molecular biology, 1994, 29(6): 415-467.). As compared with L-phosphinothricin preparation using such enzyme as transaminase, synthesis of L-phosphinothricin by reductive amination of PPO using glutamate dehydrogenase has two distinctive advantages: 1) the theoretical yield could reach 100% with a proper cofactor regeneration system; 2) use of the inorganic $NH_4^+$ as amino-group donor can avoid by-product formation, product purification is easier.

According to Patent of Invention with Publication Patent Number of CN106978453A, our team has obtained numerous glutamate dehydrogenases with reductive amination activity toward PPO applying a genome mining-based library construction strategy, and these glutamate dehydrogenases has successfully been applied for the preparation of L-phosphinothricin; acquisition of such glutamate dehydrogenases has proved the technical feasibility of this L-phosphinothricin preparation process. However, the enzyme activity of these glutamate dehydrogenases is relatively low for practical application; wherein, the highest enzyme activity (per volume of fermentation broth) of these glutamate dehydrogenase recombinant strains is only 35.54 U/L. Lower enzyme activity may bring forth a series of problems, such as high catalyst preparation cost and difficult downstream process. Therefore, enhancing of the catalytic activity of glutamate dehydrogenases toward PPO is essential for realizing industrial applications of this L-phosphinothricin preparation process.

Furthermore, glutamate dehydrogenases as obtained in aforesaid patent of invention with reductive amination activity toward PPO are all NADPH-specific, which show no activity when NADH is used as coenzyme. As compared with NADP(H), NAD(H) has distinctive advantages either in terms of stability or cost. Therefore, development of NADH-specific glutamate dehydrogenases with catalytic activity toward PPO can further reduce the production cost of L-phosphinothricin.

SUMMARY

In order to solve the problems of low glutamate dehydrogenase catalytic activity and lack of NADH-specific glutamate dehydrogenase which is catalytically active toward PPO in the L-phosphinothricin reductive amination preparation process, the present invention has conducted site-directed mutation to the amino acid residues in the substrate binding pocket of glutamate dehydrogenases. NADPH-specific glutamate dehydrogenase mutants with high catalytic activity toward PPO and NADH-specific glutamate dehydrogenase mutants that exhibited catalytic activity toward PPO were developed; this has significantly increased substrate conversion and product concentration in the L-phosphinothricin reductive amination preparation process.

Specific technical solutions are stated as follows:

The present invention provides glutamate dehydrogenase mutants with amino acid sequences as shown in SEQ ID NO.1-9, 11, 13, 15, 17-19 and 22.

The present invention further provides the coding genes for the glutamate dehydrogenase mutants according to claim 1.

The present invention further provides the expression vectors or transformants including coding gene of the glutamate dehydrogenase mutant.

The present invention has rational designed the glutamate dehydrogenase (NCBI Accession No. NP_742836.1) from *Pseudomonas putida* to enhance its catalytic activity toward 2-oxo-4-[(hydroxy)(methyl)phosphinoyl]butyric acid (PPO) by mutated the alanine (Ala167) in substrate binding pocket into glycine or mutated valine (Val378) in substrate binding pocket into alanine.

The applicant has applied this engineering method to other glutamate dehydrogenases from different sources and with different coenzyme specificity; the residues corresponding to PpGluDH's Ala167 and Val378 were targeted by sequence alignment and then mutated to glycine and alanine respectively by molecular biological method. All of the tested glutamate dehydrogenases obtained improvement in PPO-oriented catalytic activity after engineering by this method.

Specific molecular engineering steps include:

1) Using the amino acid sequence of PpGluDH as a template, the amino acid residues of microbial glutamate dehydrogenase that are corresponding to alanine-167 and valine-378 of PpGluDH are identified by sequence alignment.

2) Design mutation primers;

3) Take the plasmid with glutamate dehydrogenase gene inserted as the template for full plasmid PCR to introduce mutation;

4) Transform PCR product into *E. coli* BL21(DE3) after digestion by Dpn I;

5) Single colonies are picked and sequenced to verify whether they are positive mutants;

6) Proceed with induction culture, collect the cells, and measure the enzyme activity.

The glutamate dehydrogenases according to the present invention are derived from microorganisms, including NADH- and NADPH-specific glutamate dehydrogenase; these glutamate dehydrogenases are derived from *Pseudomonas putida, Corynebacterium glutamicum, Pseudomonas entomophila, Lysinibacillus sphaericus, Geobacillus stearothermophilus, Bacillus subtilis, Bacillus megaterium, Clostridium symbiosum* or *Brevibacillus thermoruber*; for details, please refer to Table 2 in Embodiment 2.

The present invention further provides application of the glutamate dehydrogenase mutants in catalyzing 2-oxo-4-[(hydroxy)(methyl)phosphinoyl]butyric acid or its salt for L-phosphinothricin preparation.

The present invention further provides a method for catalyzing 2-oxo-4-[(hydroxy)(methyl)phosphinoyl]butyric acid or its salt for L-phosphinothricin preparation, including:

(1) Construct the genetically engineered strain expressing glutamate dehydrogenase mutant; amino acid sequence of the glutamate dehydrogenase mutant is as shown in SEQ ID NO. 1-9, 11, 13, 15, 17-19 and 22;

(2) Culture the genetically engineered strain, and prepare enzyme solution;

(3) Add the enzyme solution into the reaction mixture containing the substrate 2-oxo-4-[(hydroxy)(methyl)phosphinoyl]butyric acid, amino donor and reduced coenzyme to start the reductive amination reaction to prepare L-phosphinothricin.

In Step (2), the said enzyme solution is resting cell suspension of genetically engineered strain or crude enzyme solution acquired by cells disruption; nevertheless, pure enzyme obtained through purification of the crude enzyme is also applicable to the method for preparation of L-phosphinothricin according to the present invention.

In a preferred embodiment, temperature of the reductive amination reaction is 15-60° C., and pH value of reaction mixture is 5-10 in Step (3).

In Step (3), the reduced coenzyme is reduced nicotinamide-adenine dinucleotide phosphate (NADPH) or reduced nicotinamide adenine dinucleotide (NADH).

In a preferred embodiment, the reaction system in Step (3) further includes a coenzyme regeneration system; the coenzyme regeneration system is stated as follows: A NAD(P)H and NAD(P)$^+$ contained glucose dehydrogenase coenzyme regeneration system taking glucose dehydrogenase as the coenzyme regeneration enzyme and glucose as the coenzyme regeneration substrate; or a NAD(P)H and NAD(P)$^+$ contained alcohol dehydrogenase coenzyme regeneration system taking alcohol dehydrogenase as the coenzyme regeneration enzyme and isopropanol as the coenzyme regeneration substrate; or NAD(P)H and NAD(P)$^+$ contained formate dehydrogenase coenzyme regeneration system taking formate dehydrogenase as the coenzyme regeneration enzyme and formate as the coenzyme regeneration substrate.

In a further preferred embodiment, the coenzyme regeneration system in the reaction system in Step (3) is a glucose dehydrogenase coenzyme regeneration system; the glucose dehydrogenase (BsGDH-2M) cloned from *Bacillus subtilis* has been molecular engineered to improved its stability; its amino acid sequence is SEQ ID NO. 21; the alcohol dehydrogenase (TBADH) is from *Thermoanaerobacter brockii*; GenBank accession number is WP_041589967.1.

Furthermore, the amino donor in Step (3) is ammonia sulfate.

As compared with prior arts, the present invention has the following beneficial effects:

(1) By means of molecular engineering, mutating the specific alanine in substrate-binding pocket into glycine and/or mutated valine in substrate-binding pocket into alanine, the present invention has significantly improved the catalytic activity of glutamate dehydrogenase toward 2-oxo-4-[hydroxy)(methyl)phosphinoyl]butyric acid (PPO), and therefore solved such problems as low glutamate dehydrogenase catalytic activity and lack of NADH-specific glutamate dehydrogenase which is catalytically active toward PPO in the L-phosphinothricin reductive amination preparation process; the applying genetically engineered strain can not only express NADPH dependent glutamate dehydrogenase with high enzyme activity, but also NADH dependent glutamate dehydrogenase with catalyzing activity to PPO, and can significantly increase substrate conversion and product concentration in L-phosphinothricin preparation process.

(2) In present invention, the PPO-oriented catalytic activity of glutamate dehydrogenases mutants was significantly improved, the highest activity increase reached 1641 times and the highest enzyme activity of per volume fermentation broth reached 34.47 U/mL; meanwhile, the NADH-specific glutamate dehydrogenase having no catalytic activity toward PPO exhibited the PPO catalytic activity after engineering; these glutamate dehydrogenase mutants exhibited high catalytic efficiency in preparation of L-phosphinothricin; the substrate conversion is >99%; maximum product concentration is up to 83.7 g/L; ee value is >99%; it has manifested a promising industrial application prospect; the present invention has successfully solved the problem of low activity of biocatalyst in the L-phosphinothricin reductive amination preparation process, which has laid down a solid foundation for industrial application of this process.

(3) The glutamate dehydrogenase mutants described in present invention not only significantly improve the catalytic activity of NADPH-specific glutamate dehydrogenases toward PPO, but also endow NADH-specific glutamate dehydrogenases the catalytic activity toward PPO, which has high academic and application value.

BRIEF DESCRIPTION OF THE DRAWINGS

Wherein, FIG. 2A is the positive mass chromatogram for PPO; FIG. 2B is the negative mass chromatogram for PPO.

Wherein, FIG. 3A is the 13C NMR spectrogram for PPO; FIG. 3B is the 1H NMR spectrogram for PPO.

Wherein, retention time is stated as follows: 6.3 min for L-phosphinothricin and 7.2 min for D-phosphinothricin.

Figure 6:
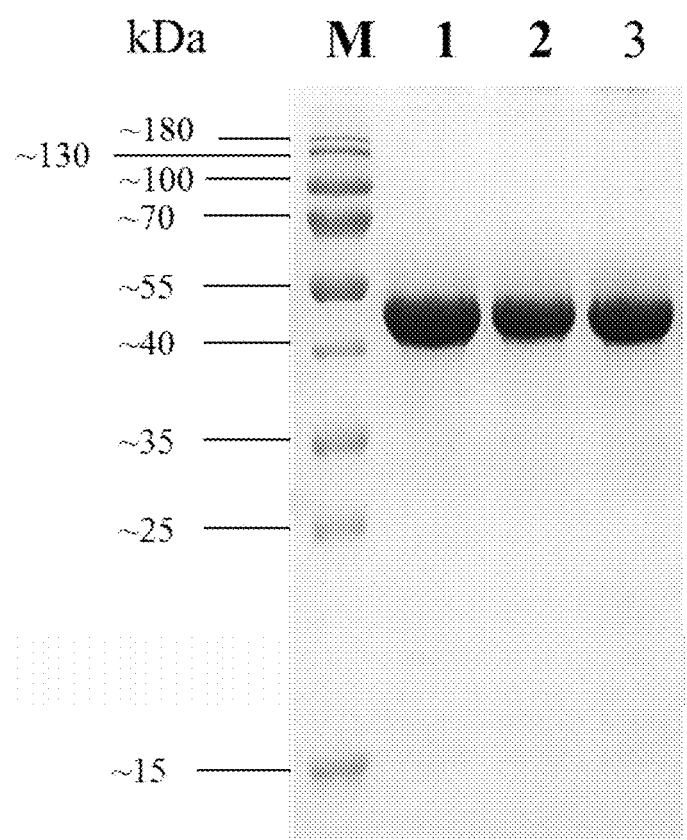

FIG. 6 shows protein purification results of PpGluDH wild type and mutants in Embodiment 1;

M: protein marker; 1: PpGluDH wild type; 2: A167G; 3: V378A ○

Figure 7:
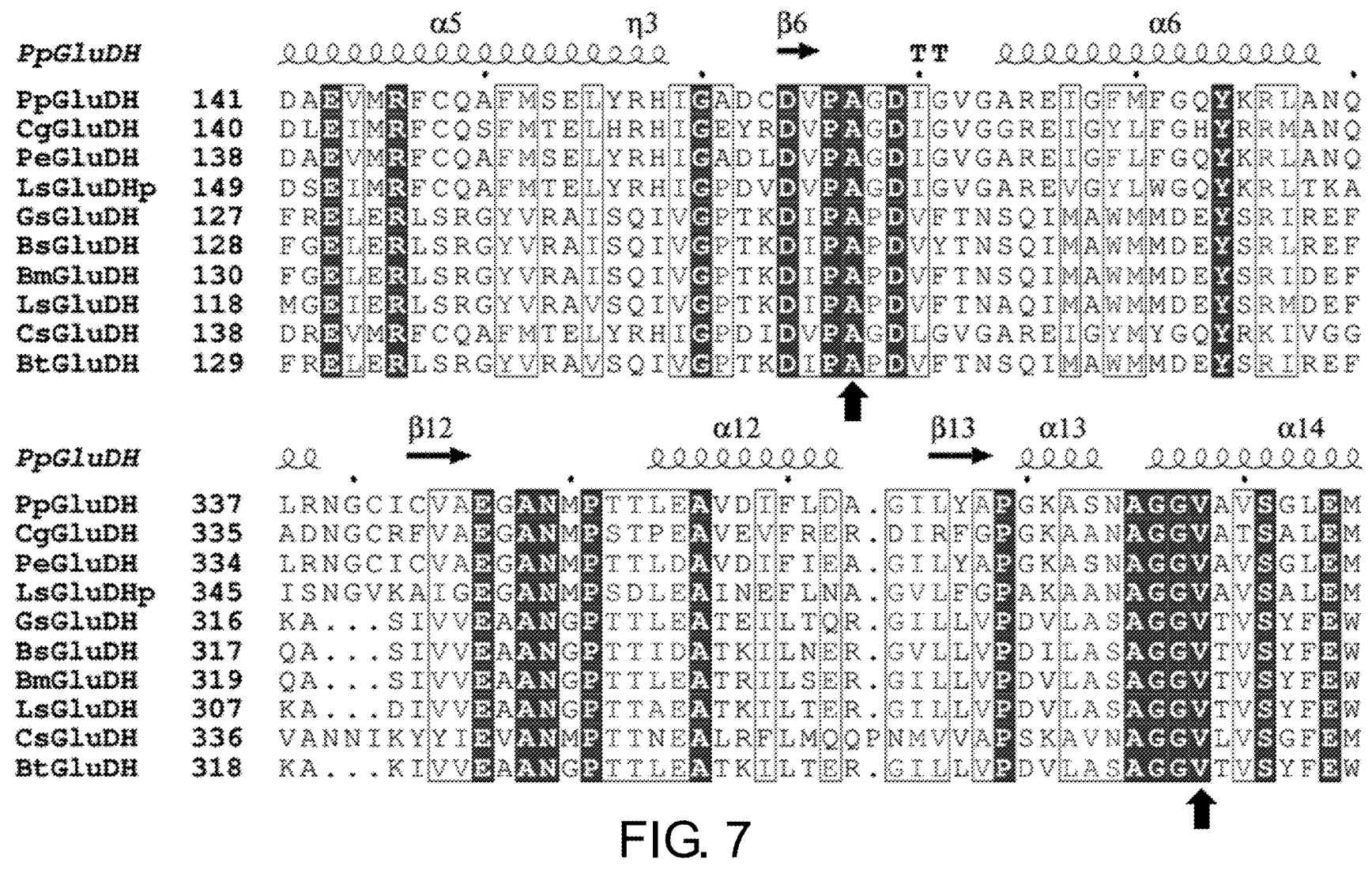

FIG. 7 shows multiple sequence alignment result of the glutamate dehydrogenases in Embodiment 2;

Wherein, A167 and V378 (PpGluDH numbering) are marked with black arrow.

Figure 8:
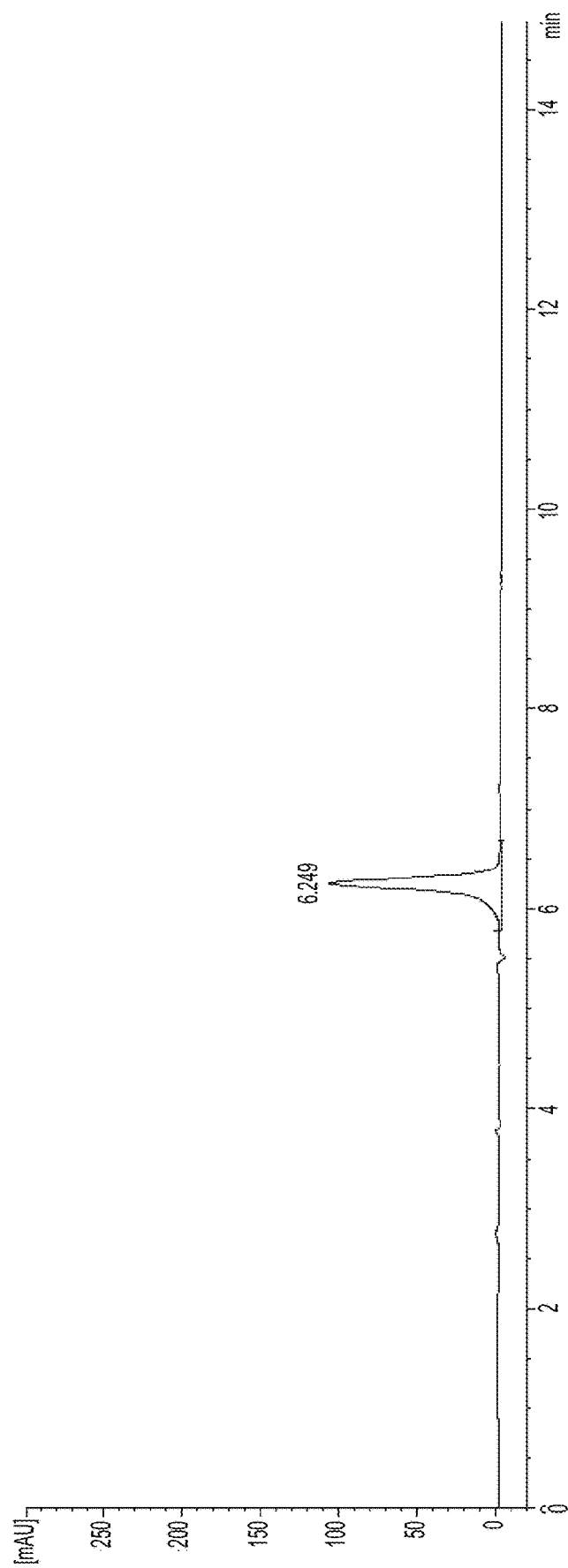

FIG. 8 is the pre-column derivatization HPLC spectrum (chiral analysis) of the reaction solution (after reaction) in Embodiment 7.

DESCRIPTION OF THE EMBODIMENTS

The present invention is further described as follows in combination with preferred embodiments. It is to be understood that the following embodiments only aim to explain the present invention, which will not restrict the scope of the present invention.

Unless specified otherwise, experiment methods as stated in the present invention are conventional methods; for gene cloning, please refer to *Molecular Cloning: A Laboratory Manual* by J. Sambrook et al.

Reagents for genetic engineering operations: DNA polymerase (PrimeSTAR® Max DNA Polymerase) and Dpn I used in embodiments of the present invention were purchased from TaKaRa, Bio (Dalian, China) Co., Ltd; Plasmid Miniprep Kit was purchased from Axygen Co., Ltd (Hangzhou, China); *E. coli* BL21(DE3), plasmid and so on are purchased from Novagen; primer synthesis and gene sequencing were carried out by TsingKe Bio-Tech Co., Ltd (Hangzhou, China). For use method of aforesaid reagents, please refer to product specifications.

The recombinant *E. coli* carrying glutamate dehydrogenase gene used in the present invention is constructed and kept by our laboratory. The vector used is pET-28a(+), and the host used is *E. coli* BL21(DE3). NI-NTA resin (HisPur™ Ni-NTA Resin) used for protein purification is purchased from Thermo Scientific™; protein purification is carried out in reference to specifications.

Figure 1:
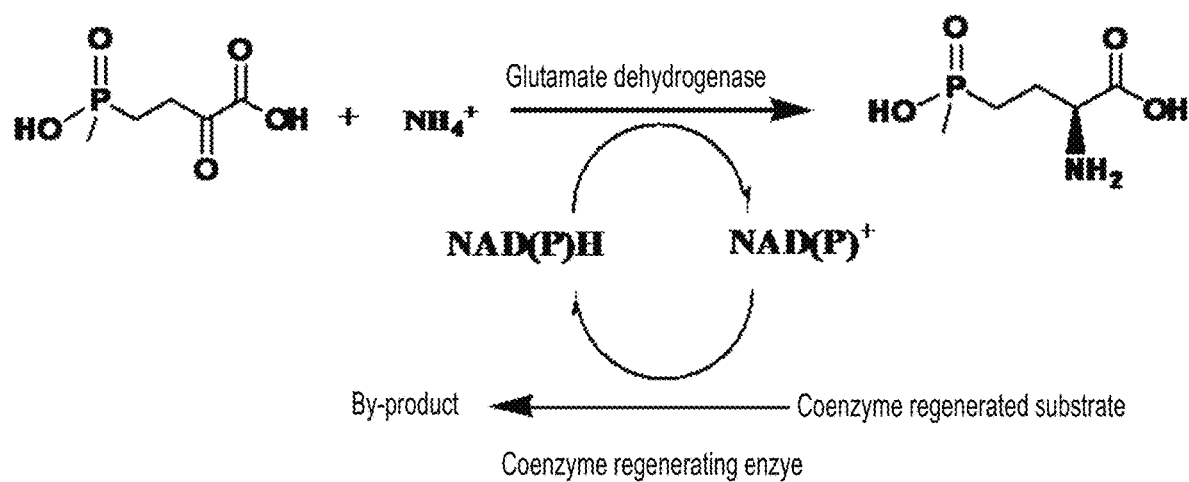
FIG. 1 is the reaction formula of L-phosphinothricin preparation using the double enzyme coupling system containing glutamate dehydrogenase and coenzyme regenerated enzyme.
Figure 2A:
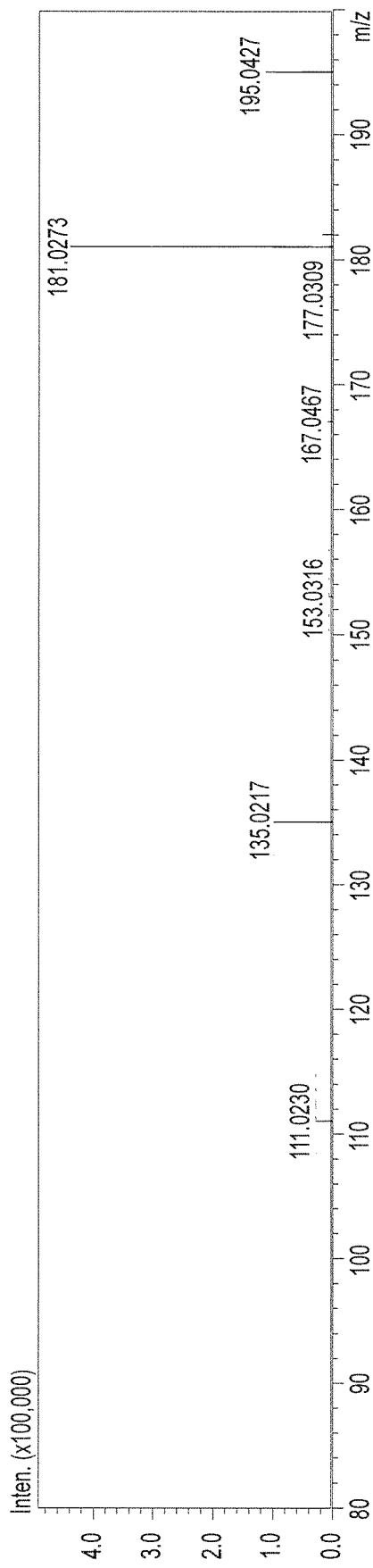
FIGS. 2A and 2B are the mass chromatogram for the material, 2-carbonyl-4-(hydroxymethyl phosphonyl) butyric acid (PPO)
Figure 2B:
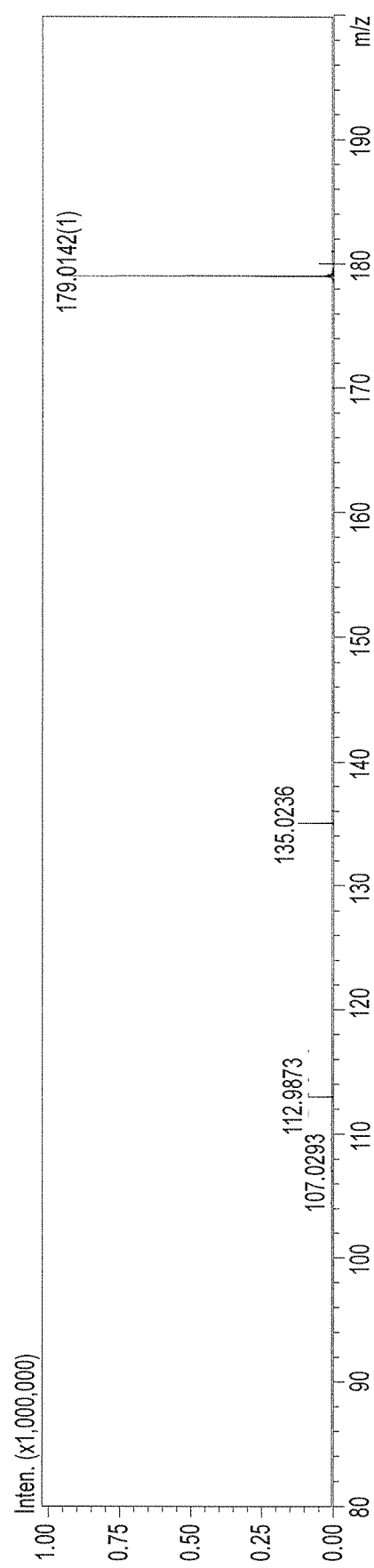
Figure 3A:
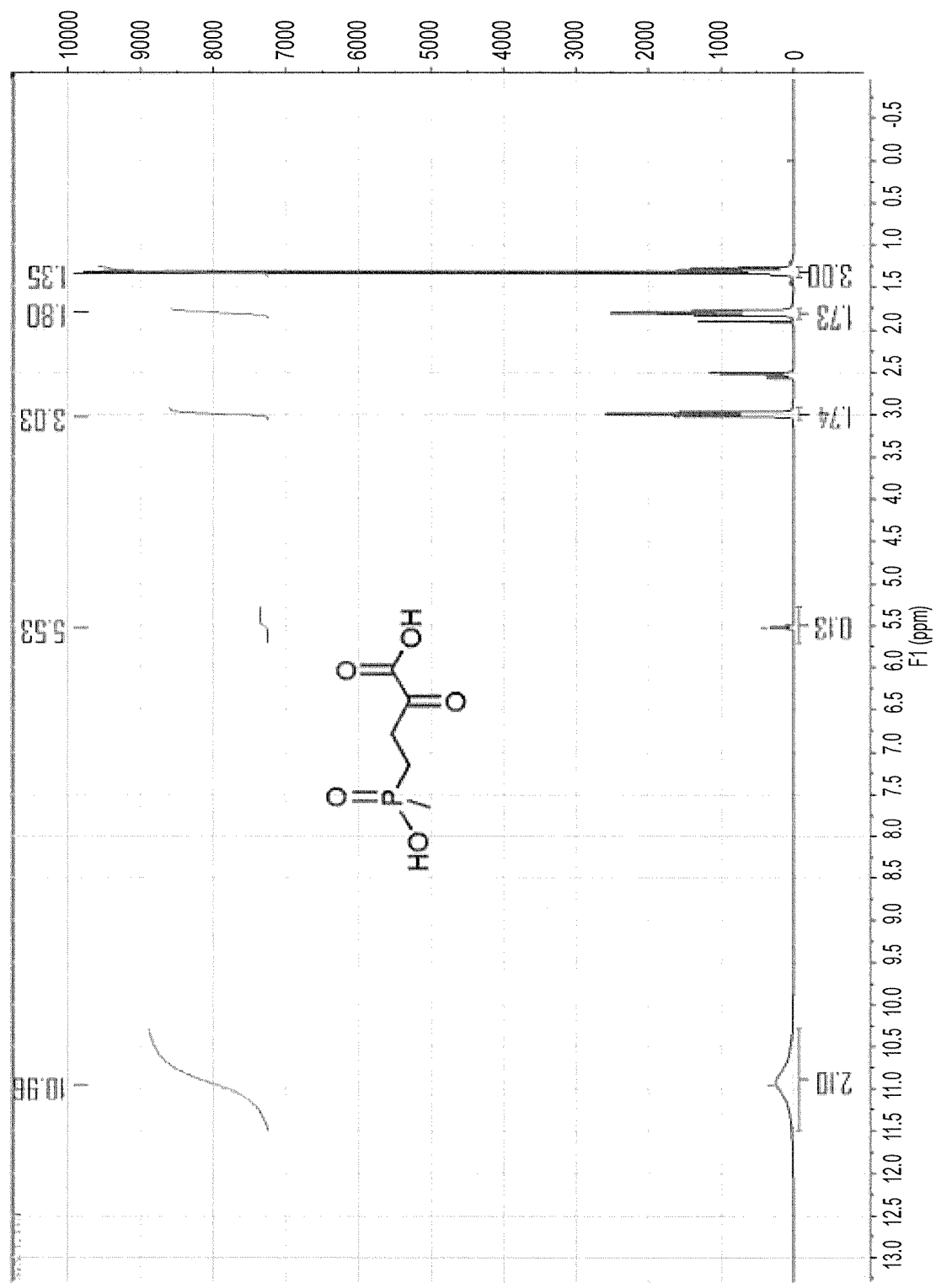
FIGS. 3A and 3B are the nuclear magnetic diagram for the material, 2-carbonyl-4-(hydroxymethyl phosphonyl) butyric acid (PPO)
Figure 3B:
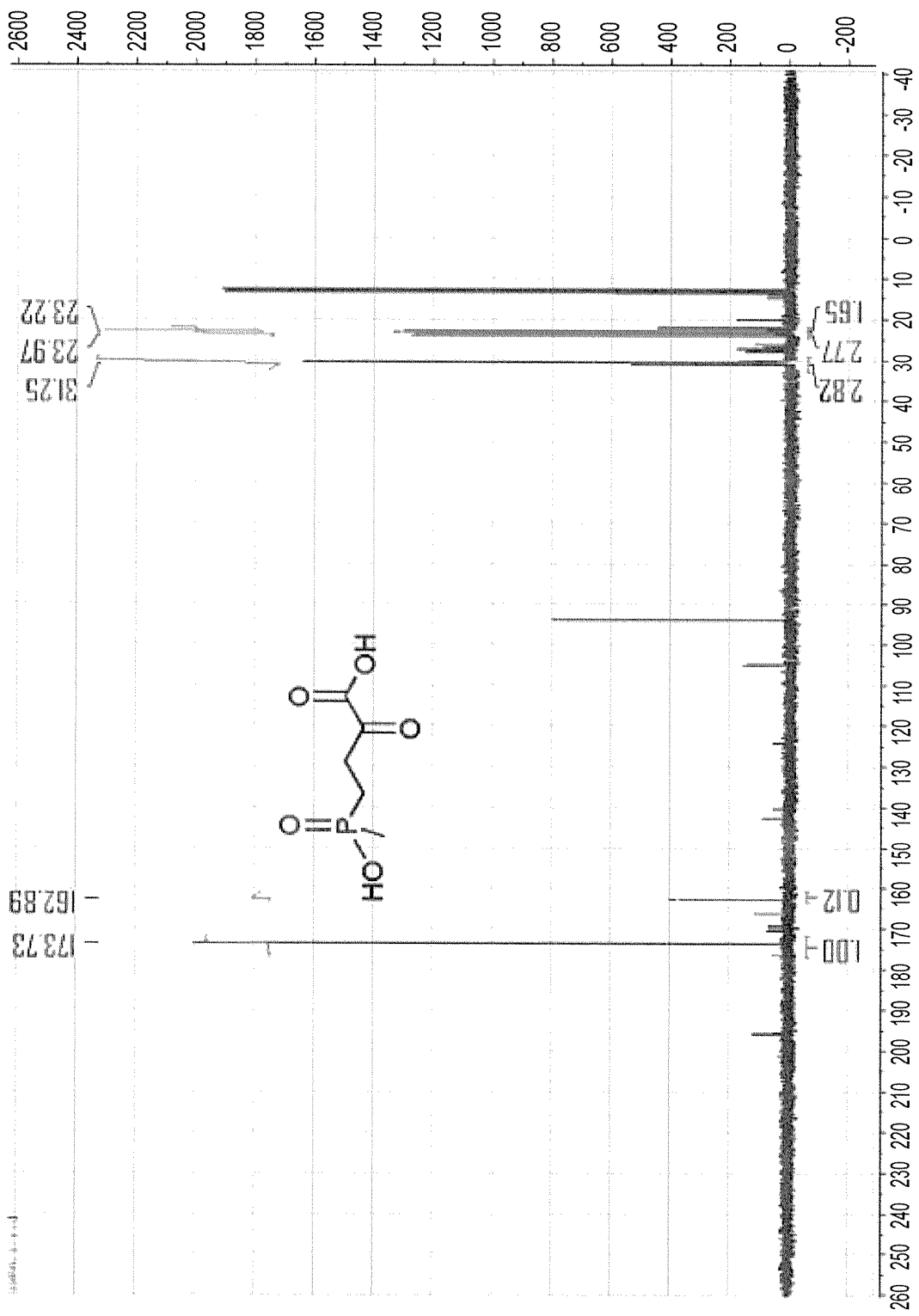

Reagents used for catalytic process: 2-oxo-4-[hydroxy) (methyl)phosphinoyl]butyric acid (PPO) is artificially synthesized, of which MS spectra and NMR spectra are as shown in FIGS. 2 and 3; standard sample of D,L-phosphinothricin is purchased from Sigma-Aldrich; $NAD^+$, $NADP^+$, NADH and NADPH are purchased from Bontac Bio-engineering Co., Ltd (Shenzhen, China); other conventional reagents are purchased from Sinopharm Chemical Reagent Co., Ltd (Shanghai, China). Three-letter or single-letter expression of amino acid used in the application text is the amino acid codes as specified by IUPAC (Eur. J. Biochem., 138:9-37,1984).

Figure 4:
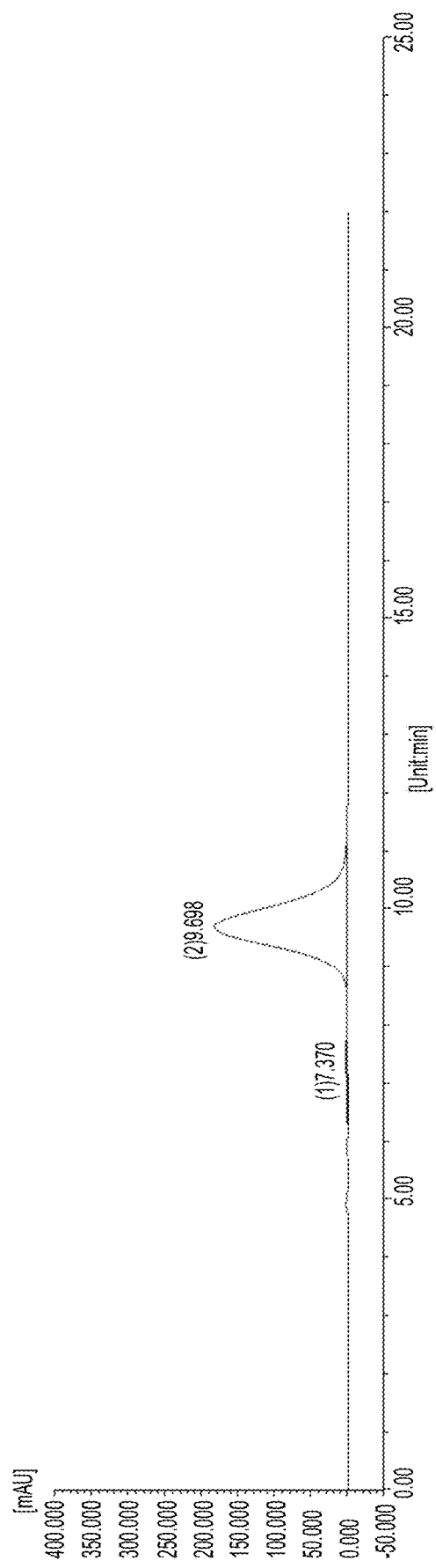
FIG. 4 is the HPLC spectrum (non-chiral analysis, 5 mM) of 2-oxo-4-[hydroxy)(methyl)phosphinoyl]butyric acid (PPO) standard sample; wherein the retention time of PPO is 9.7 min.

The reaction process is monitored by measuring the concentration of substrate in the reaction solution applying high-performance liquid chromatography (HPLC). HPLC analysis method is stated as follows: column model: Pntulips® QS-C18, 5 μm, 4.6 mm×250 mm. Mobile phase: 50 mM $(NH_4)_2HPO_4$, added 1% of 10% tetrabutyl ammonium hydroxide, adjusted to pH 3.6 with 50% phosphoric acid (mass fraction), added 8% acetonitrile. Detective wave length is 205 nm; flow rate is 1.0 mL/min. Column temperature is 40° C. The retention time of substrate is as shown in FIG. 4.

The enantiomeric excess and concentration of product are determined through pre-column derivatization high-performance liquid chromatography; the specific analysis method is stated as follows:

(1) HPLC condition: column model: Pntulips® QS-C18, 5 μm, 4.6 mm×250 mm. Mobile phase: 50 mM Sodium acetate: Acetonitrile=8: 0.5 (v/v). Detective wave length: 338 nm. Flow rate: 0.85 mL/min. Column temperature: 30° C.

(2) Derivatization reagent: Weigh 0.03 g phthalaldehyde and 0.1 g N-acetyl-L-cysteine, and use 400 uL ethanol for solubilization; after that, add 4 mL 0.2 mol/L borate buffer (pH 9.8) and shake for dissolution prior to storage in the fridge under the temperature of 4° C. (no more than 4 days).

(3) Derivatization reaction and analysis: Add 150 μL derivatization reagent into 100 μL sample, mix and incubate at 25° C. for 5 min, and then inject 20 μL for analysis.

Figure 5:
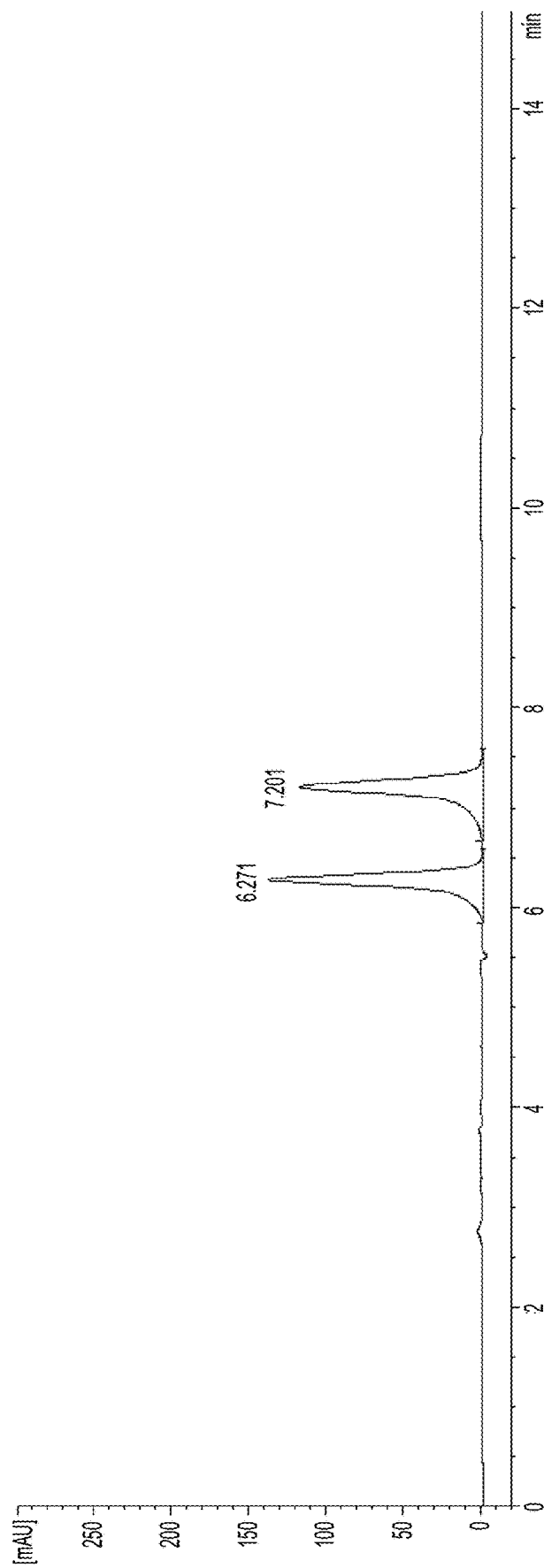
FIG. 5 is the pre-column derivatization HPLC spectrum (chiral analysis, 2 mM) of standard samples of racemic phosphinothricin.

The retention time of D-phosphinothricin and L-phosphinothricin is as shown in FIG. 5.

Embodiment 1

Engineering of Glutamate Dehydrogenase from *Pseudomonas putida* and Catalytic Activity Determination Step 1: Activation of Recombinant Strain and Plasmid Extraction Use LB medium for activation and culture of recombinant *Escherichia coli* carrying the gene of glutamate dehydrogenase from *Pseudomonas putida* (PpGluDH) (NCBI Accession No.: NP_742836.1).

Specific formula for LB culture medium is stated as follows: peptone 10 g/L, yeast powder 5 g/L, NaCl 10 g/L, dissolved in deionized water, and then sterilized at 121° C. for 20 min. Solid culture medium is formed by adding 2% agar into LB liquid medium.

The preserved PpGluDH recombinant strain is streaked onto the plate containing LB solid medium, and culture at 37° C. for 12 h. Single colony is picked and inoculated into 5 mL LB liquid medium containing 50 μg/mL kanamycin, and then cultured at 200 rpm under the temperature of 37° C. for 12 h. Once the culture is obtained, the plasmid is extracted according to specifications of plasmid extraction kit. The plasmid obtained can be directly used for follow-up operations or store at −20° C. for a long time.

Step 2: Site-Directed Mutagenesis

Design specific primers (Table 1), mutate the alanine at 167-site and the valine at 378-site in the amino acid sequence of PpGluDH to glycine (A167G) and alanine (V378A), respectively.

TABLE 1

Primers for Site-directed Mutation of PpGluDH

| Primer | Sequence (5' to 3')[a] |
|---|---|
| A167G-F | ACGTACCGGGTGGTGACATCGGTGTGGGGG SEQ ID NO. 23 |
| A167G-R | ATGTCACCACCCGGTACGTCGCAGTCAGCA SEQ ID NO. 24 |
| V378A-F | CGGGCGGCGCAGCCGTGTCGGGCCTGGAAA SEQ ID NO. 25 |
| V378A-R | GACACGGCTGCGCCGCCCGCATTGGAGGCC SEQ ID NO. 26 |

Note:
underlined codon encodes desired amino acid substitution

Take plasmid extracted in previous step as the template, and use Quickchange site-directed mutagenesis protocol (An efficient one-step site-directed and site-saturation mutagenesis protocol[J]. Nucleic Acids Research, 2004, 32(14): e115) to introduce mutation; the PCR system and conditions are stated as follows:

PCR System:

| | |
|---|---|
| DNA polymerase | 25 μL; |
| Upstream primer (10 pmol/μL) | 1.5 μL; |
| Downstream primer (10 pmol/μL) | 1.5 μL; |
| Plasmid template | 1.0 μL; |
| ddH$_2$O | 21 μL. |

PCR Conditions:
1) Pre-denaturation: 98° C. 2 min;
2) Denaturation: 98° C. 15 s; annealing: 58° C. 10 s; elongation: 72° C. 2 min; total 30 cycles;
3) Extension: 72° C. 10 min;
4) Storage under the temperature of 4° C.

After PCR amplification, the amplified product is digested with Dpn I for 3 h to remove the template plasmids; the digestion product is transformed into *E. coli* BL21(DE3) competent cell, and then plated on LB agar plates. Pick single colonies to LB medium for culture, and then sequence to verify the correctness of the mutation. The positive mutants are stored at −80° C. until for further use.

Step 3: Cell Culture and Crude Enzyme Preparation

The preserved recombinant *E. coli* is streaked onto the plate for activation. Single colonies are picked and inoculated into 5 mL LB liquid medium containing 50 μg/mL kanamycin and cultured at 37° C. for 12 h. The culture is transferred to 50 mL fresh LB liquid medium containing 50 μg/mL kanamycin at a 2% inoculum, and then incubated at 37° C. until the OD$_{600}$ reaches 0.6; after that, add IPTG to a final concentration of 0.5 mM, and then proceed with induction culture under the temperature of 18° C. for 16 h.

After the cultivation, the culture is centrifuged at 10000 rpm for 10 min; discard supernatant, and collect cells. The harvested cells are washed for 2 times using pH 7.5 50 mM phosphate buffer. After that, the cells are re-suspend into the pH 7.5 phosphate buffer and disrupted ultrasonically (400W for 30 times, Ultrasonic time is 3 s, and the interval is 7 s). The cell disrupted solution is centrifuged at 12000 g for 5 min at 4° C. to remove the precipitate, and the supernatant obtained is the crude enzyme containing recombinant glutamate dehydrogenase Step 4: Measurement of Enzyme Activity The standard enzyme activity measurement system: Appropriate amount of enzyme, 100 mM substrate, 10 mM coenzyme (NADH or NADPH), 500 mM NH$_4^+$ ((NH$_4$)$_2$SO$_4$); total system volume is up to 400 μL; reaction medium is pH 7.5 phosphate buffer. 35° C. reaction for 10 min; after that, add 40 uL 5 M NaOH to terminate reaction.

Definition of enzyme activity unit: The quantity of enzyme as required by generation of 1 μmol L-phosphinothricin per minute under standard reaction conditions.

Enzyme activity (per volume fermentation broth) of wild type PpGluDH and mutants (PpGluDH-A167G and PpGluDH-V378A) obtained by the aforesaid engineering method has been measured with aforesaid enzyme activity measurement method. Enzyme activity of wild type PpGluDH is 0.11 U/mL; Enzyme activity of PpGluDH-A167G is 14.85 U/mL, which is 135 times higher than that of wild type; activity of PpGluDH-V378A is 13.3 U/mL, which is 121 times higher than that of wild type.

Meanwhile, specific activity of pure enzyme obtained through purification has also been measured. As measured, specific activity of pure protein of wild type PpGluDH is 0.31 U/mg; specific activity of PpGluDH-A167G is 38.13 U/mg, which is 123 times higher than that of wild type; specific activity of PpGluDH-V378A is 35.96 U/mg, which is 116 times higher than that of wild type.

Step 5: Construction of Combinatorial Mutant and Measurement of Enzyme Activity

Proceed with activation and plasmid extraction for PpGluDH-A167G mutant; after that, mutation is introduced by Quickchange site-directed mutagenesis protocol using primer V378A-F/V378A-R; specific methods are as shown in Step 2; combinatorial mutant of PpGluDH-A167G/V378A (SEQ ID NO. 22) has been constructed. Induction culture of the combinatorial mutant strain has been carried out as per Step 3 and Step 4, and enzyme activity has been measured. As measured, enzyme activity (per volume fermentation broth) of PpGluDH-A167G/VA78A is 13.85 U/mL, which is 126 times higher than that of wild type.

Comparative Embodiment 1

The catalytic activity of wild type PpGluDH and mutants toward other keto acid substrates has been measured by spectrophotometry. Compared with the wild type, mutants have exhibited reduced catalytic activity to most of substrates (2-8a, 10-11a and 13a) For 2-ketoglutarate (1 a) and 2-ketohexanoic acid (9a), PpGluDH-A167G and PpGluDH-V378A have exhibited improved catalytic activity; for 2-oxo-4-phenylbutyric acid (12a), catalytic activity of PpGluDH-A167G has been improved to some extent; whereas catalytic activity of PpGluDH-V378A decreased.

TABLE 2

Catalytic activity of wild type PpGluDH and mutants toward other keto acid substrates

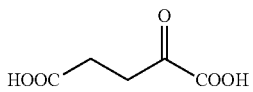

1a

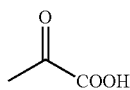

2a

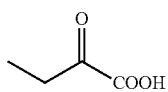

3a

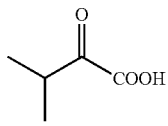

4a

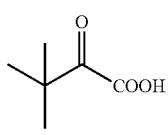

5a

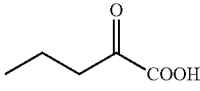

6a

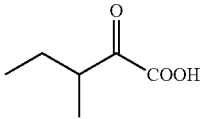

7a

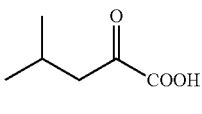

8a

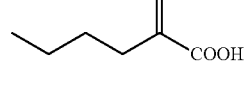

9a

TABLE 2-continued

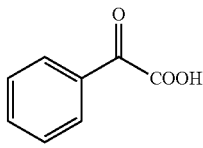 [SMILES: O=C(O)C(=O)c1ccccc1]

10a

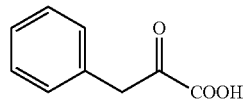 [SMILES: O=C(O)C(=O)Cc1ccccc1]

11a

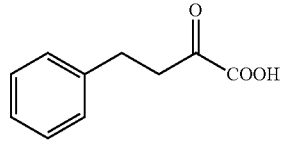 [SMILES: O=C(O)C(=O)CCc1ccccc1]

12a

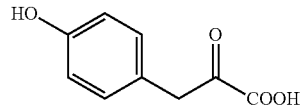 [SMILES: O=C(O)C(=O)Cc1ccc(O)cc1]

13a

|  | Specific activity (U/mg) | | |
| --- | --- | --- | --- |
| Substrate | Wild | A167G | V378A |
| 2-Ketoglutaric acid (1a) | 189.05 | 314.41 | 268.48 |
| Pyruvic acid (2a) | 0.15 | <0.01 | 0.01 |
| 2-Ketobutyric acid (3a) | 4.93 | 0.09 | 0.34 |
| 3-Methyl-2-oxobutanoic acid (4a) | 0.37 | <0.01 | 0.04 |
| 3,3-Dimethyl-2-oxo-butanoic acid (5a) | NA$^a$ | NA$^a$ | NA$^a$ |
| 2-Oxovaleric acid (6a) | 6.39 | 1.21 | 2.37 |
| 3-Methyl-2-Oxovaleric acid (7a) | 0.07 | <0.01 | 0.03 |
| 4-Methyl-2-Oxovaleric acid (8a) | 0.05 | 0.01 | 0.03 |
| 2-Ketohexanoic acid (9a) | 0.71 | 1.23 | 1.49 |
| Phenylglyoxylic acid (10a) | 0.04 | 0.01 | 0.01 |
| Phenylpyruvic acid (11a) | <0.01 | <0.01 | <0.01 |
| 2-Oxo-4-phenylbutyric acid (12a) | 0.08 | 0.33 | 0.04 |
| 4-hydroxyphenylpyruvic acid (13a) | 0.02 | <0.01 | <0.01 |

Embodiment 2

Step 1: Selection of Glutamate Dehydrogenases

Select 9 glutamate dehydrogenases of different sources, different coenzyme specificity and different homology with PpGluDH to perform the same protein engineering (for details, please refer to Table 2). Wherein, CgGluDH, PeGluDH and LsGluDH belong to NADPH-specific glutamate dehydrogenases; GsGluDH, BsGluDH, BmGluDH, LsGluDH, CsGluDH and BtGluDH belong to NADH-specific glutamate dehydrogenases.

TABLE 2

The GluDHs selected for applicability evaluation

| Designation | Source | Homology (%) | NCBI Accession No. | Coenzyme Specificity |
|---|---|---|---|---|
| PpGluDH | pseudomonas putida | 100 | NP_742836.1 | NADPH |
| CgGluDH | corynebacterium glutamicum | 59.0 | NP_601279.1 | |
| PeGluDH | Pseudomonas entomophila | 93.8 | WP_044487662.1 | |
| LsGluDHp | Lysinibacillus sphaericus | 54.8 | WP_012293812.1 | |
| GsGluDH | Geobacillus stearothermophilus | 29.8 | WP_033013982.1 | NADH |
| BsGluDH | Bacillus subtilis | 28.8 | NP_391659.2 | |
| BmGluDH | Bacillus megaterium | 28.2 | WP_013084905.1 | |
| LsGluDH | Lysinibacillus sphaericus | 29.8 | WP_012292398.1 | |
| CsGluDH | Clostridium symbiosum | 53.4 | WP_003497202.1 | |
| BtGluDH | Brevibacillus thermoruber | 29.7 | WP_029099571.1 | |

Note:
The sequence homology was measured with the amino acid sequence of PpGluDH as reference.

Step 2: Identification of Corresponding Mutation Sites and Construction of Mutants Use online software T-Coffee for multiple sequence alignment to target amino acid residues (FIG. 7) of each glutamate dehydrogenase corresponding to the Ala167 and Val378 of PpGluDH. The amino acid sequence of the glutamate dehydrogenases shown in FIG. 7 are respectively from *Pseudomonas putida* (PpGluDH) (NCBI Accession No.: NP_742836.1), *Corynebacterium glutamicum* (CgGluDH) (NCBI Accession No.: NP_601279.1), *Pseudomonas entomophila* (PeGluDH) (NCBI Accession No.: WP_044487662.1), *Lysinibacillus sphaericus* (LsGluDH) (NCBI Accession No.: WP_012293812.1), *Geobacillus stearothermophilus* (GsGluDH) (NCBI Accession No.: WP_033013982.1), *Bacillus subtilis* (BsGluDH) (NCBI Accession No.: NP_391659.2), *Bacillus megaterium* (BmGluDH) (NCBI Accession No.: WP_013084905.1), *Lysinibacillus sphaericus* (LsGluDH) (NCBI Accession No.: WP_012292398.1), *Clostridium symbiosum* (CsGluDH) (NCBI Accession No.: WP_003497202.1) and *Brevibacillus thermoruber* (BtGluDH) (NCBI Accession No.: WP_029099571.1).

From the alignment result, it can be found that the two amino acid residues (FIG. 7) of all the glutamate dehydrogenases corresponding to PpGluDH are alanine and valine; this indicates that these two amino acid residues are highly conserved among the glutamate dehydrogenases. These two residues of selected glutamate dehydrogenases were mutated to glycine and alanine, respectively; for detail information of the mutants to be constructed, please refer to Table 3. Proceed with construction of mutant according to Step 1 and 2 in Embodiment 1.

TABLE 3

Glutamate dehydrogenase mutants to be constructed

| Designation | Mutant | Codon variation (Before mutation→after mutation) | Amino acid sequence |
|---|---|---|---|
| CgGluDH | A166G | GCA→GGT | SEQ ID NO. 3 |
| | V376A | GTT→GCA | SEQ ID NO. 4 |
| PeGluDH | A164G | GCC→GGT | SEQ ID NO. 5 |
| | V375A | GTG→GCA | SEQ ID NO. 6 |
| LsGluDHp | A175G | GCT→GGT | SEQ ID NO. 7 |
| | V386A | GTT→GCA | SEQ ID NO. 8 |
| GsGluDH | A153G | GCG→GGT | SEQ ID NO. 9 |
| | V354A | GTG→GCA | SEQ ID NO. 10 |
| BsGluDH | A154G | GCT→GGT | SEQ ID NO. 11 |
| | V355A | GTC→GCA | SEQ ID NO. 12 |
| BmGluDH | A156G | GCG→GGT | SEQ ID NO. 13 |
| | V357A | GTA→GCA | SEQ ID NO. 14 |
| LsGluDH | A144G | GCA→GGT | SEQ ID NO. 15 |
| | V345A | GTT→GCA | SEQ ID NO. 16 |
| CsGluDH | A164G | GCA→GGT | SEQ ID NO. 17 |
| | V378A | GTT→GCA | SEQ ID NO. 18 |
| BtGluDH | A155G | GCA→GGT | SEQ ID NO. 19 |
| | V356A | GTA→GCA | SEQ ID NO. 20 |

Step 3: Construction of Mutants and Measurement of Enzyme Activity

Proceed with induction culture of constructed mutants, and prepare crude enzyme solution. Catalytic activity of such mutants toward PPO has been measured based on standard enzyme activity measurement system; results are as shown in Table 4.

TABLE 4

Enzyme activity measurement result of the mutants

| Designation | Enzyme activity of wild type (U/mL) | Mutant | Enzyme activity of mutants (U/mL) | Fold change |
|---|---|---|---|---|
| CgGluDH | 0.011 | A166G | 0.34 | 31 |
| | | V376A | 2.48 | 225 |
| PeGluDH | 0.103 | A164G | 11.29 | 110 |
| | | V375A | 11.06 | 107 |
| LsGluDHp | 0.021 | A175G | 34.47 | 1641 |
| | | V386A | 12.34 | 588 |
| GsGluDH | N.D. | A153G | 0.04 | — |
| | | V354A | N.D. | — |
| BsGluDH | N.D. | A154G | 0.50 | — |
| | | V355A | N.D. | — |

TABLE 4-continued

Enzyme activity measurement result of the mutants

| Designation | Enzyme activity of wild type (U/mL) | Mutant | Enzyme activity of mutants (U/mL) | Fold change |
|---|---|---|---|---|
| BmGluDH | N.D. | A156G | 0.34 | — |
|  |  | V357A | N.D. | — |
| LsGluDH | N.D. | A144G | 1.69 | — |
|  |  | V345A | N.D. | — |
| CsGluDH | N.D. | A164G | 2.61 | — |
|  |  | V378A | 1.76 | — |
| BtGluDH | N.D. | A155G | 0.50 | — |
|  |  | V356A | N.D. | — |

Note:
N.D. = no detectable activity

From the results of the enzyme activity measurement, it can be found that for NADPH-specific glutamate dehydrogenases, both A167G and V378A mutations (PpGluDH numbering) could significantly improve the catalytic activity toward PPO, and the highest activity increase is up to 1641-fold.

For NADH-specific glutamate dehydrogenases, mutation of A167G ((PpGluDH numbering) could increase their PPO activity from zero of wild type to considerable values.

Embodiment 3

Preparation of L-phosphinothricin by Coupling Wild Type Glutamate Dehydrogenase (PpGluDH) with Glucose Dehydrogenase Culture recombinant E. coli expressing glutamate dehydrogenase (PpGluDH) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NADP^+$. Concentration of glutamate dehydrogenase cells (dry weight) is 1.0 g/L; concentration of glucose dehydrogenase cells (dry weight) is 1.25 g/L. Use water bath to control the reaction temperature at 35° C.; titrate ammonia to control pH at 7.5 during the reaction process. Use non-chiral HPLC to determine residual concentration of PPO after reaction for 6 h; meanwhile, use pre-column derivatization HPLC to determine the concentration and ee value of formed L-phosphinothricin.

Data upon completion of reaction is stated as follows: residual PPO is 447 mM; substrate conversion is 10.6%. The concentration of formed L-phosphinothricin is 8.7 g/L; ee value >99%.

Embodiment 4

Preparation of L-phosphinothricin by Coupling Glutamate Dehydrogenase Mutant (PpGluDH-A167G) with Glucose Dehydrogenase Culture recombinant E. coli expressing glutamate dehydrogenase (PpGluDH-A167G, SEQ ID NO. 1) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NADP^+$. Concentration of glutamate dehydrogenase cells (dry weight) is 1.0 g/L; concentration of glucose dehydrogenase cells (dry weight) is 1.25 g/L. Use water bath to control the reaction temperature at 35° C.; titrate ammonia to control pH at 7.5 during the reaction process. Use non-chiral HPLC to determine residual concentration of PPO after reaction for 6 h; meanwhile, use pre-column derivatization HPLC to determine the concentration and ee value of formed L-phosphinothricin.

Data upon completion of reaction is stated as follows: residual PPO is 0.9 mM; substrate conversion is 99.8%. The concentration of formed L-phosphinothricin is 83.7 g/L; ee value >99%.

Embodiment 5

Preparation of L-phosphinothricin by Coupling Glutamate Dehydrogenase Mutant (PpGluDH-V378A) with Glucose Dehydrogenase Culture recombinant E. coli expressing glutamate dehydrogenase (PpGluDH-V378AG, SEQ ID NO. 2) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NADP^+$. Concentration of glutamate dehydrogenase cells (dry weight) is 1.0 g/L; concentration of glucose dehydrogenase cells (dry weight) is 1.25 g/L. Use water bath to control the reaction temperature at 35° C.; titrate ammonia to control pH at 7.5 during the reaction process. Use non-chiral HPLC to determine residual concentration of PPO after reaction for 6 h; meanwhile, use pre-column derivatization HPLC to determine the concentration and ee value of formed L-phosphinothricin.

Data upon completion of reaction is stated as follows: residual PPO is 1.2 mM; substrate conversion is 99.8%. The concentration of formed L-phosphinothricin is 81.9 g/L; ee value >99%.

Embodiment 6

Preparation of L-phosphinothricin by Coupling Wild Type Glutamate Dehydrogenase (LsGluDHp) with Glucose Dehydrogenase Culture recombinant E. coli expressing glutamate dehydrogenase (LsGluDHp) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NADP^+$. Concentration of glutamate dehydrogenase cells (dry weight) is 0.5 g/L; concentration of glucose dehydrogenase cells (dry weight) is 1.25 g/L. Use water bath to control the reaction temperature at 35° C.; titrate ammonia to control pH at 7.5 during the reaction process. Use non-chiral HPLC to determine residual concentration of PPO after reaction for 6 h; meanwhile, use pre-column derivatization HPLC to determine the concentration and ee value of formed L-phosphinothricin.

Data upon completion of reaction is stated as follows: residual PPO is 481 mM; substrate conversion is 3.8%. The concentration of formed L-phosphinothricin is 0.87 g/L; ee value >99%.

Embodiment 7

Preparation of L-phosphinothricin by Coupling Glutamate Dehydrogenase Mutant (LsGluDHp-A175G) with Glucose Dehydrogenase Culture recombinant E. coli expressing glutamate dehydrogenase (LsGluDHp-A175G, SEQ ID NO. 7) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NADP^+$. Concentration of glutamate dehydrogenase cells (dry weight) is 0.5 g/L; concentration of glucose dehydrogenase cells (dry weight) is 1.25 g/L. Use water bath to control the reaction temperature at 35° C.; titrate ammonia to control pH at 7.5 during the reaction process. Use non-chiral HPLC to determine residual concentration of PPO after reaction for 6 h; meanwhile, use pre-column derivatization HPLC to determine the concentration and ee value of formed L-phosphinothricin.

Data upon completion of reaction is stated as follows: residual PPO is 0 mM; substrate conversion is 100%. The concentration of formed L-phosphinothricin is 82.4 g/L; ee value >99%.

Embodiment 8

Preparation of L-phosphinothricin by Coupling Glutamate Dehydrogenase Mutant (LsGluDHp-A175G) with Alcohol Dehydrogenase Culture recombinant E. coli expressing glutamate dehydrogenase (LsGluDHp-A175G, SEQ ID NO. 7) and alcohol dehydrogenase (TBADH, WP_041589967.1) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 750 mM isopropanol, 250 mM $(NH_4)_2SO_4$ and 0.5 mM $NADP^+$. Concentration of glutamate dehydrogenase cells (dry weight) is 0.5 g/L; concentration of alcohol dehydrogenase cells (dry weight) is 2.5 g/L. Use water bath to control the reaction temperature at 35° C.; titrate ammonia to control pH at 7.5 during the reaction process. Use non-chiral HPLC to determine residual concentration of PPO after reaction for 12 h; meanwhile, use pre-column derivatization HPLC to determine the concentration and ee value of formed L-phosphinothricin.

Data upon completion of reaction is stated as follows: residual PPO is 1.3 mM; substrate conversion is 99.7%. The concentration of formed L-phosphinothricin is 81.3 g/L; ee value >99%.

Embodiment 9

Preparation of L-phosphinothricin by Coupling Wild Type Glutamate Dehydrogenase (CsGluDH) with Glucose Dehydrogenase Culture recombinant E. coli expressing glutamate dehydrogenase (CsGluDH) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NAD^+$. Concentration of glutamate dehydrogenase cells (dry weight) is 1.25 g/L; concentration of glucose dehydrogenase cells (dry weight) is 1.25 g/L. Use water bath to control the reaction temperature at 35° C.; titrate ammonia to control pH at 7.5 during the reaction process. Use non-chiral HPLC to determine residual concentration of PPO after reaction for 6 h; meanwhile, use pre-column derivatization HPLC to determine the concentration and ee value of formed L-phosphinothricin.

Data upon completion of reaction is stated as follows: residual PPO is 491.3 mM; substrate conversion is 1.7%. The concentration of formed L-phosphinothricin is 1.63 g/L; ee value >99%.

Embodiment 10

Preparation of L-phosphinothricin by Coupling Glutamate Dehydrogenase Mutant (CsGluDH-A164G) with Glucose Dehydrogenase Culture recombinant E. coli expressing glutamate dehydrogenase (CsGluDH-A164G, SEQ ID NO. 17) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NAD^+$. Concentration of glutamate dehydrogenase cells (dry weight) is 1.25 g/L; concentration of glucose dehydrogenase cells (dry weight) is 1.25 g/L. Use water bath to control the reaction temperature at 35° C.; titrate ammonia to control pH at 7.5 during the reaction process. Use non-chiral HPLC to determine residual concentration of PPO after reaction for 6 h; meanwhile, use pre-column derivatization HPLC to determine the concentration and ee value of formed L-phosphinothricin.

Data upon completion of reaction is stated as follows: residual PPO is 0 mM; substrate conversion is 100%. The concentration of formed L-phosphinothricin is 79.6 g/L; ee value >99%.

Embodiment 11

Preparation of L-phosphinothricin by Coupling Glutamate Dehydrogenase Mutant (CsGluDH-V378A) with Glucose Dehydrogenase Culture recombinant E. coli expressing glutamate dehydrogenase (CsGluDH-V378A, SEQ ID NO. 18) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NAD^+$. Concentration of glutamate dehydrogenase cells (dry weight) is 1.25 g/L; concentration of glucose dehydrogenase cells (dry weight) is 1.25 g/L. Use water bath to control the reaction temperature at 35° C.; titrate ammonia to control pH at 7.5 during the reaction process. Use non-chiral HPLC to determine residual concentration of PPO after reaction for 12 h; meanwhile, use pre-column derivatization HPLC to determine the concentration and ee value of formed L-phosphinothricin.

Data upon completion of reaction is stated as follows: residual PPO is 1.8 mM; substrate conversion is 99.6%. The concentration of formed L-phosphinothricin is 78.5 g/L; ee value >99%.

Embodiment 12

Preparation of L-phosphinothricin by Coupling Wild Type Glutamate Dehydrogenase (BtGluDH) with Glucose Dehydrogenase Culture recombinant *E. coli* expressing glutamate dehydrogenase (BtGluDH) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NAD^+$. Concentration of glutamate dehydrogenase cells (dry weight) is 1.25 g/L; concentration of glucose dehydrogenase cells (dry weight) is 1.25 g/L. Use water bath to control the reaction temperature at 50° C.; titrate ammonia to control pH at 7.5 during the reaction process. Use non-chiral HPLC to determine residual concentration of PPO after reaction for 6 h; meanwhile, use pre-column derivatization HPLC to determine the concentration and ee value of formed L-phosphinothricin.

Data upon completion of reaction is stated as follows: residual PPO is 493.1 mM; substrate conversion is 1.4%. The concentration of formed L-phosphinothricin is 0 g/L; ee value >99%.

Embodiment 13

Preparation of L-phosphinothricin by Coupling Glutamate Dehydrogenase Mutant (BtGluDH-A155G) with Glucose Dehydrogenase Culture recombinant *E. coli* expressing glutamate dehydrogenase (BtGluDH-A155G, SEQ ID NO. 19) and glucose dehydrogenase (BsGDH-2M, SEQ ID NO. 21) with method in Step 3 of Embodiment 1; proceed with centrifugal collection of cells and ultrasonic cell disruption to prepare crude enzyme solution.

The final volume of the reaction is 30 mL; each sample contains 500 mM substrate PPO, 600 mM glucose, 250 mM $(NH_4)_2SO_4$ and 0.5 mM $NAD^+$. Concentration of glutamate dehydrogenase cells (dry weight) is 1.25 g/L; concentration of glucose dehydrogenase cells (dry weight) is 1.25 g/L. Use water bath to control the reaction temperature at 50° C.; titrate ammonia to control pH at 7.5 during the reaction process. Use non-chiral HPLC to determine residual concentration of PPO after reaction for 6 h; meanwhile, use pre-column derivatization HPLC to determine the concentration and ee value of formed L-phosphinothricin.

Data upon completion of reaction is stated as follows: residual PPO is 1.4 mM; substrate conversion is 99.7%. The concentration of formed L-phosphinothricin is 80.3 g/L; ee value >99%.

What is claimed is:

1. A method of catalyzing 2-oxo-4-[(hydroxy)(methyl)phosphinoyl]butyric acid or its salt for L-phosphinothricin preparation, comprising:
    (1) Prepare genetically engineered strain expressing glutamate dehydrogenase mutant; amino acid sequence of the glutamate dehydrogenase mutant is SEQ ID NO. 1, 2, 5, 7 and 8;
    (2) Culture the genetically engineered strain, and prepare enzyme solution;
    (3) Add the enzyme solution into a reaction system containing the substrate 2-oxo-4-[(hydroxy)(methyl)phosphinoyl]butyric acid, amino donor and reduced coenzyme to start a reductive amination reaction to prepare L-phosphinothricin.

2. The method according to claim 1, wherein in Step (3) temperature of the reductive amination reaction is 15-60° C., and pH value of the reaction mixture is 5-10.

3. The method according to claim 1, wherein in Step (3) the reduced coenzyme is NADPH or NADH.

4. The method according to claim 1, wherein the reaction system in Step (3) further comprises:
    coenzyme regeneration enzyme, comprising glucose dehydrogenase, alcohol dehydrogenase or formate dehydrogenase; and
    coenzyme regeneration substrate, comprising glucose, isopropanol or formate,
    wherein the reduced coenzyme includes NAD(P)H and NAD(P)$^+$.

5. The method according to claim 4, wherein the coenzyme regeneration system in the reaction system is a glucose dehydrogenase coenzyme regeneration system; amino sequence of the glucose dehydrogenase is SEQ ID NO. 21.

6. The method according to claim 1, wherein the amino donor in Step (3) is ammonia sulfate.

* * * * *